(12) United States Patent
Bae et al.

(10) Patent No.: US 11,766,444 B2
(45) Date of Patent: Sep. 26, 2023

(54) PHARMACEUTICAL COMPOSITION FOR PREVENTING OR TREATING DEGENERATIVE BRAIN DISORDERS INCLUDING HDL-APOM-S1P AS ACTIVE INGREDIENT

(71) Applicant: Kyungpook National University Industry-Academic Cooperation Foundation, Daegu (KR)

(72) Inventors: Jae Sung Bae, Daegu (KR); Hee Kyung Jin, Daegu (KR); Ju Youn Lee, Daegu (KR); Min Hee Park, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 580 days.

(21) Appl. No.: 16/634,460

(22) PCT Filed: Jul. 11, 2018

(86) PCT No.: PCT/KR2018/007857
§ 371 (c)(1),
(2) Date: Jan. 27, 2020

(87) PCT Pub. No.: WO2019/022412
PCT Pub. Date: Jan. 31, 2019

(65) Prior Publication Data
US 2021/0085697 A1  Mar. 25, 2021

(30) Foreign Application Priority Data

Jul. 28, 2017  (KR) .................. 10-2017-0096223

(51) Int. Cl.
*A61K 31/661* (2006.01)
*A61K 47/69* (2017.01)
*A61P 25/28* (2006.01)

(52) U.S. Cl.
CPC ........ *A61K 31/661* (2013.01); *A61K 47/6917* (2017.08); *A61P 25/28* (2018.01)

(58) Field of Classification Search
CPC .............. A61K 31/661; A61K 47/6917; A61K 9/1275; A61K 9/0019; A61K 47/42; A61P 25/28
See application file for complete search history.

(56) References Cited

U.S. PATENT DOCUMENTS 9,592,268 B2 *  3/2017  Hla ......................... A61P 9/10
2014/0303086 A1  10/2014  Hla et al.

FOREIGN PATENT DOCUMENTS

| JP | 2012532919 A | 12/2012 |
| KR | 100588241 B1 | 6/2006 |
| KR | 101132636 B1 | 4/2012 |
| WO | 2012162392 A1 | 11/2012 |

OTHER PUBLICATIONS

Sattler, K., "Defects of high-density lipoproteins in coronary artery disease caused by low sphingosine-1-phosphate content: correction by sphingosine-1-phosphate—loading." Journal of the American College of Cardiology 66.13 (2015): 1470-1485; Supplemental Information p. 1-13.*
Sattler, K., "Defects of high-density lipoproteins in coronary artery disease caused by low sphingosine-1-phosphate content: correction by sphingosine-1-phosphate—loading." Journal of the American College of Cardiology 66.13 (2015): 1470-1485.*
Sattler, K., "Defects of high-density lipoproteins in coronary artery disease caused by low sphingosine-1-phosphate content: correction by sphingosine-1-phosphate—loading." Journal of the American College of Cardiology 2015 Supplemental Methods p. 1-13.*
Trenova, A. G., "Cognitive impairment in multiple sclerosis." Folia medica 58.3 (2016): 157-163.*
Chan, Hua-Chen et al., MEDLINE / NLM, Nov. 26, 2020, NLM33256187, Taiwan.
International Search Report issued by ISA/KR in connection with PCT/KR2018/007857 dated Nov. 23, 2018.
Malaplate-Armand, Catherine et al., Soluble Oligomers of Amyloid-Beta Peptide Induce Neuronal Apoptosis by Activating a cPLA2-dependent Sphingomyelinase-ceramide Pathway, Neurobiology of Disease, 2006, pp. 178-189, vol. 23. Elsevier, France.
Hajny, S. et al., A Novel Perspective on the ApoM-S1P Axis, Highlighting the Metabolism of ApoM and Its Role in Liver Fibrosis and Neuroinflammation, International Journal of Molecular Sciences, Jul. 27, 2017, pp. 1-19, vol. 18, No. 1636.
Pyne, S. et al., Sphingosine 1-phosphate and Sphingosine Kinases in Health and Disease: Recent Advances, Progress in Lipid Research, 2016, pp. 93-106, vol. 62, Elsevier.

(Continued)

*Primary Examiner* — John M Mauro
(74) *Attorney, Agent, or Firm* — Levenfeld Pearlstein, LLC

(57) ABSTRACT

The present invention relates to a novel use for HDL-ApoM-S1P (a high density lipoprotein in which apolipoprotein M is impregnated with sphingosine-1-phosphate), and more particularly, to using HDL-ApoM-S1P to prevent, improve, or treat degenerative brain disorders (in particular, Alzheimer's disease), cognitive disorders, learning disabilities, and memory disorders, and using HDL-ApoM-S1P to improve cognitive ability, learning ability, and memory.
The HDL-ApoM-S1P according to the present invention not only alleviates neuroinflammation but also significantly exhibits improvement effects of cognitive disorder, learning disability, and memory disorder with respect to individuals suffering from degenerative brain disorders (in particular, Alzheimer's disease), and exhibits an effect of greatly reducing amyloid beta and tau deposition. Moreover, increased HDL-ApoM-S1P in the body also has an excellent effect of improving the cognitive, learning, and memory abilities of non-disabled individuals.

2 Claims, 27 Drawing Sheets
(10 of 27 Drawing Sheet(s) Filed in Color)
Specification includes a Sequence Listing.

(56) References Cited

OTHER PUBLICATIONS

Maceyka, M. et al., Sphingosine-1-phosphate Signaling and Its Role in Disease, Trends in Cell Biology, 2012, pp. 50-60, vol. 22, No. 1, Elsevier.
Couttas, Timothy A. et al., Loss of the Neuroprotective Factor Sphingosine 1-phosphate Early in Alzheimer's Disease Pathogenesis, Acta Neuropathologica Communications, 2014, pp. 1-13, vol. 2, No. 9.
Ruiz, Mario et al., HDL-associated ApoM Is Anti-apoptotic by Delivering Sphingosine 1-phosphate to S1P1 & S1P3 Receptors on Vascular Endothelium, Lipids in Health and Disease, Feb. 8, 2017, pp. 1-12, vol. 16, No. 36.
Written Opinion issued by ISA/KR in connection with PCT/KR2018/007857 dated Nov. 23, 2018.

\* cited by examiner

APP/PS1

APP/PS1+HDL/ApoM/S1P

APP/PS1+S1P

APP/PS1+ApoM

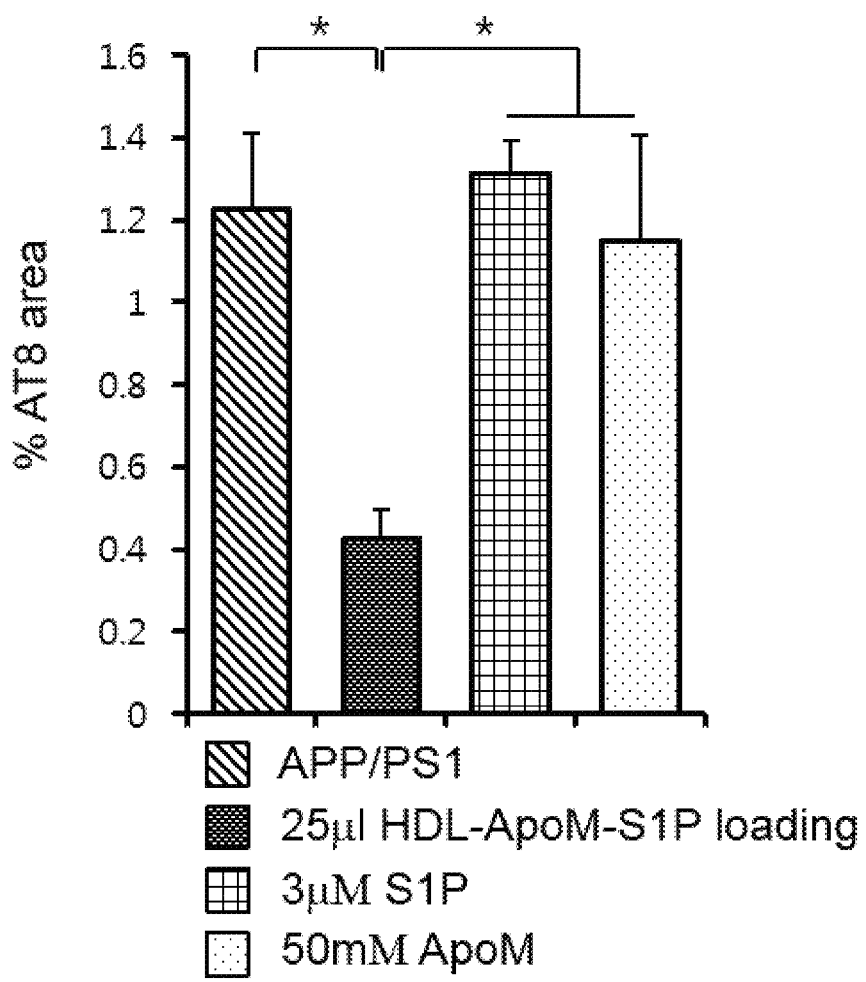

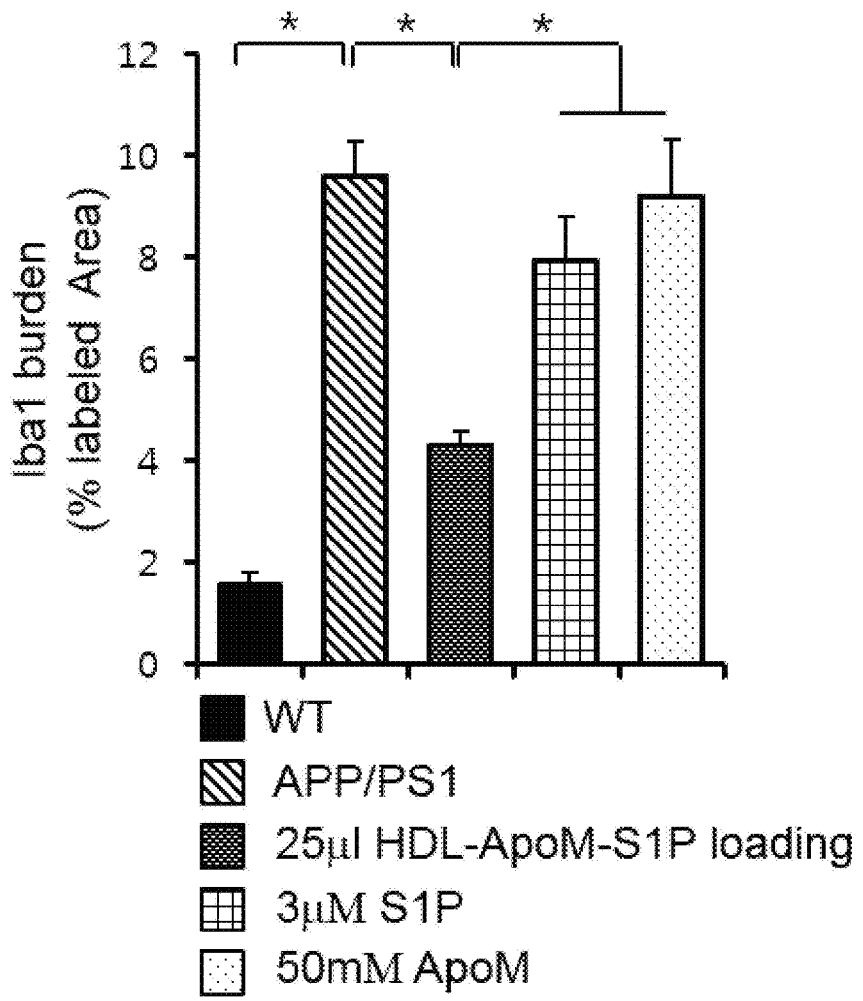

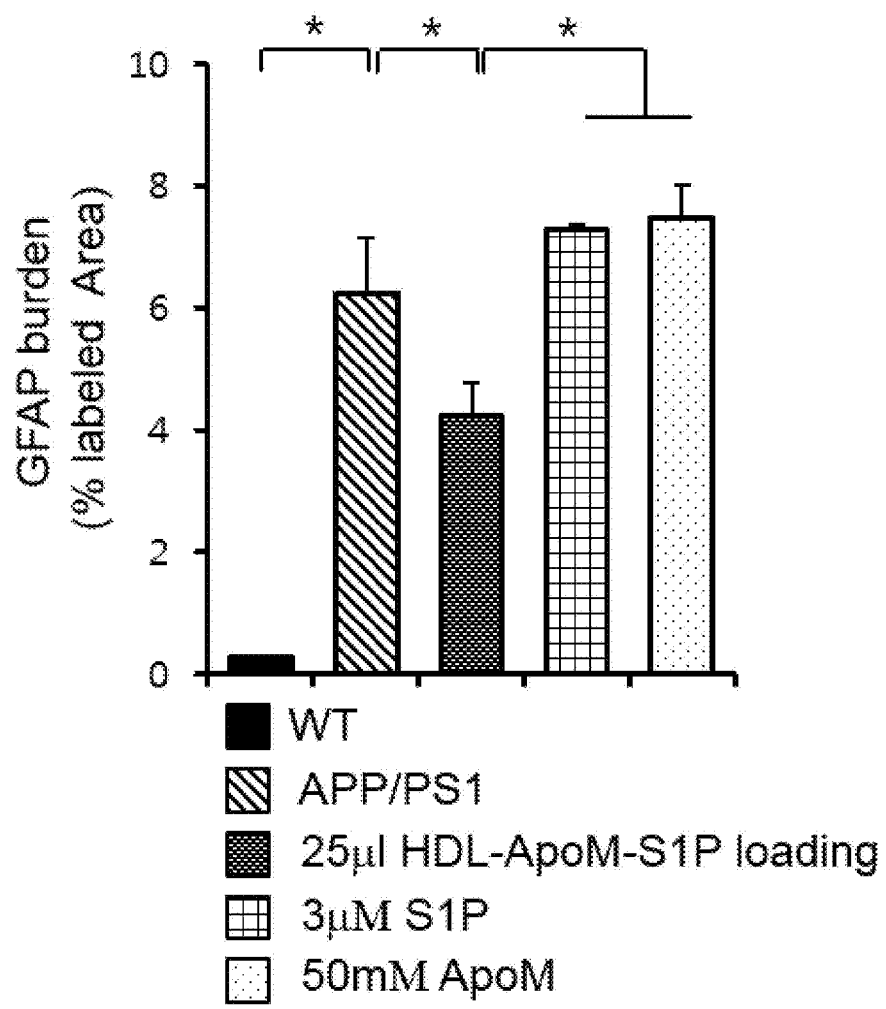

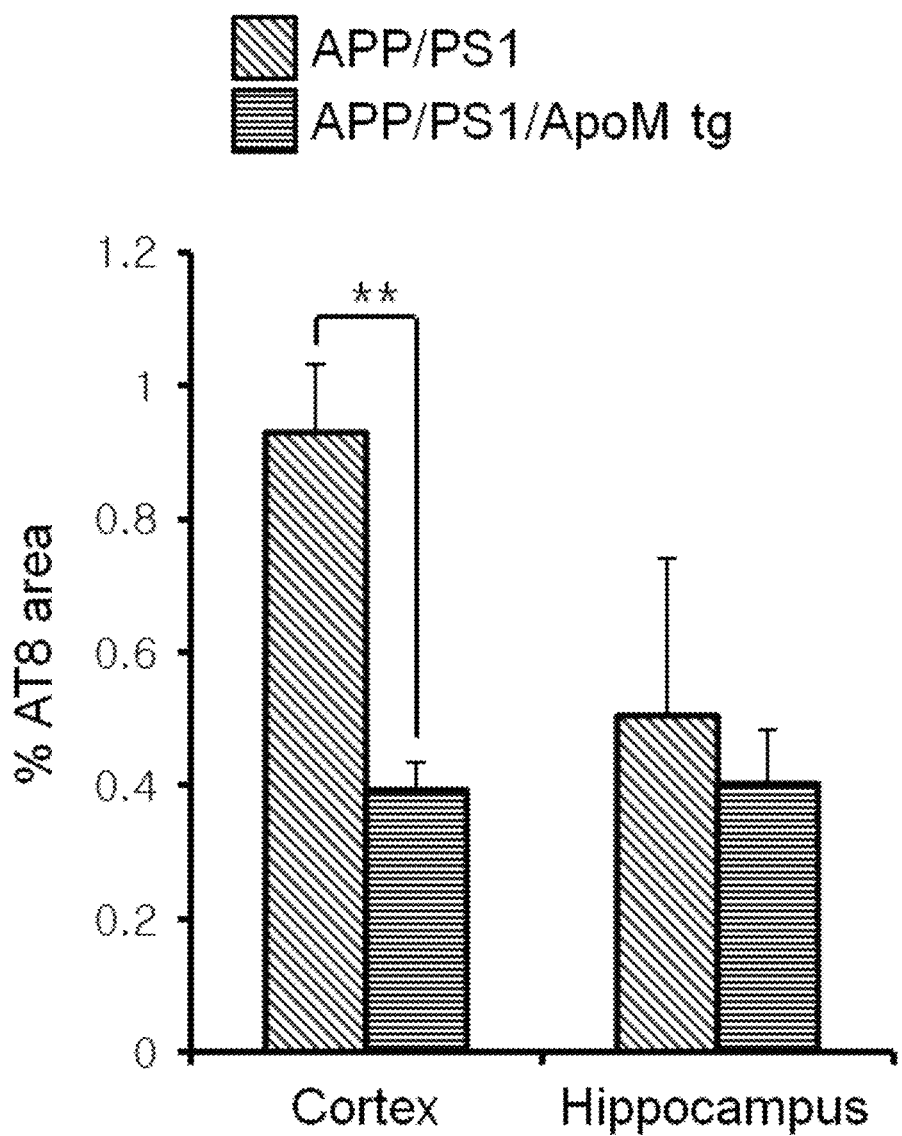

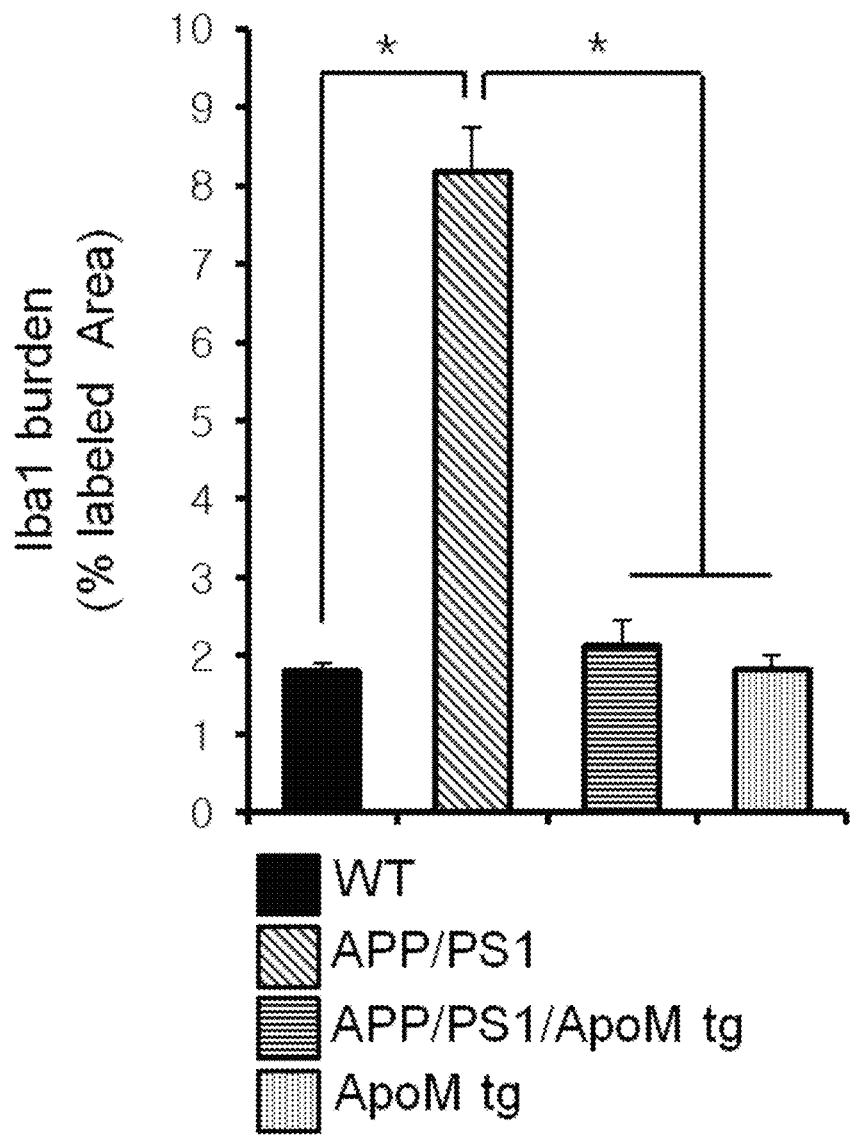

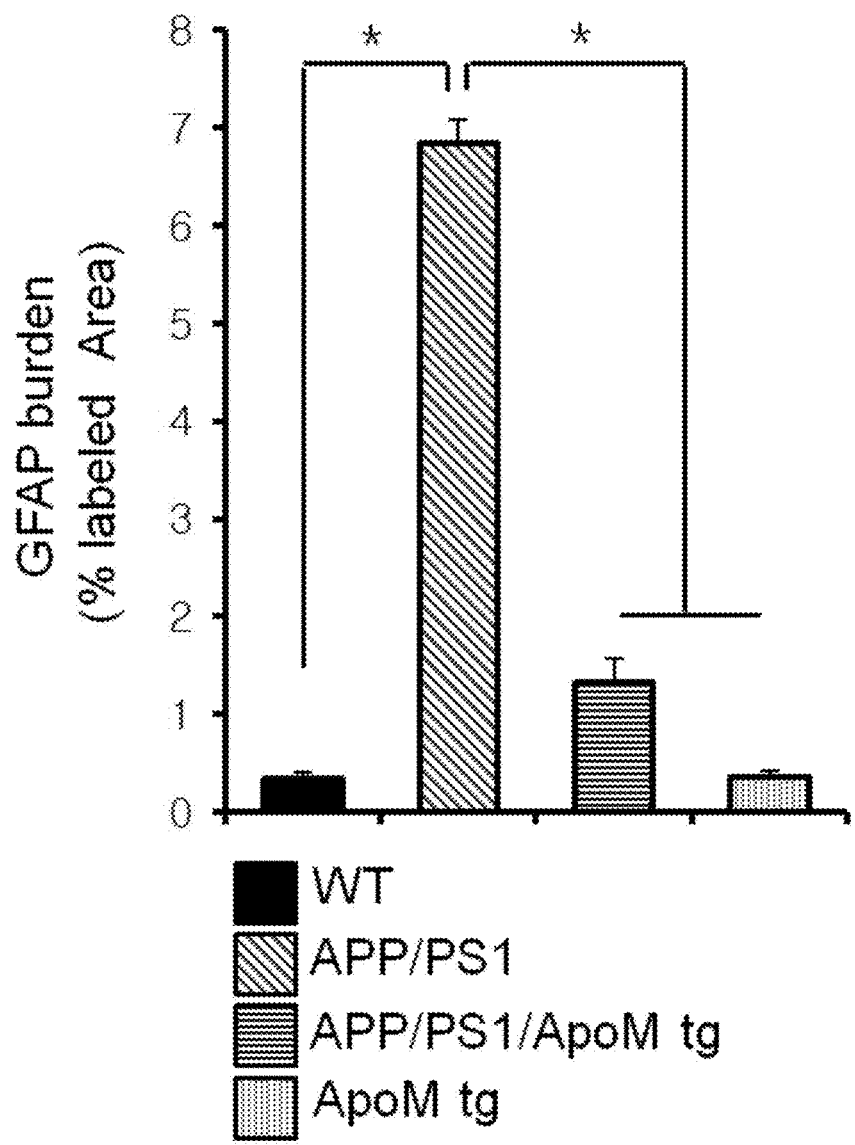

SEQUENCE LISTING

```
<160> NUMBER OF SEQ ID NOS: 1

<210> SEQ ID NO 1
<211> LENGTH: 188
<212> TYPE: PRT
<213> ORGANISM: Artificial Sequence
<220> FEATURE:
<223> OTHER INFORMATION: ApoM

<400> SEQUENCE: 1

Met Phe His Gln Ile Trp Ala Ala Leu Leu Tyr Phe Tyr Gly Ile Ile
1               5                   10                  15

Leu Asn Ser Ile Tyr Gln Cys Pro Glu His Ser Gln Leu Thr Thr Leu
                20                  25                  30

Gly Val Asp Gly Lys Glu Phe Pro Glu Val His Leu Gly Gln Trp Tyr
            35                  40                  45

Phe Ile Ala Gly Ala Ala Pro Thr Lys Glu Glu Leu Ala Thr Phe Asp
    50                  55                  60

Pro Val Asp Asn Ile Val Phe Asn Met Ala Ala Gly Ser Ala Pro Met
65                  70                  75                  80

Gln Leu His Leu Arg Ala Thr Ile Arg Met Lys Asp Gly Leu Cys Val
                85                  90                  95

Pro Arg Lys Trp Ile Tyr His Leu Thr Glu Gly Ser Thr Asp Leu Arg
                100                 105                 110

Thr Glu Gly Arg Pro Asp Met Lys Thr Glu Leu Phe Ser Ser Ser Cys
            115                 120                 125

Pro Gly Gly Ile Met Leu Asn Glu Thr Gly Gln Gly Tyr Gln Arg Phe
    130                 135                 140

Leu Leu Tyr Asn Arg Ser Pro His Pro Pro Glu Lys Cys Val Glu Glu
145                 150                 155                 160

Phe Lys Ser Leu Thr Ser Cys Leu Asp Ser Lys Ala Phe Leu Leu Thr
                165                 170                 175

Pro Arg Asn Gln Glu Ala Cys Glu Leu Ser Asn Asn
                180                 185
```

PHARMACEUTICAL COMPOSITION FOR PREVENTING OR TREATING DEGENERATIVE BRAIN DISORDERS INCLUDING HDL-APOM-S1P AS ACTIVE INGREDIENT

CROSS-REFERENCE TO RELATED APPLICATIONS

This is a National Stage Application of International Patent Application No. PCT/KR2018/007857, filed Jul. 11, 2018, which claims the benefit of and priority to Korean Patent Application No. 10-2017-0096223, filed Jul. 28, 2017, the contents of which are incorporated fully by reference herein.

TECHNICAL FIELD

This application claims priority from Korean Patent Application No. 10-2017-0096223, filed on Jul. 28, 2017, the entire contents of which are incorporated herein by reference.

The present invention relates to a novel use for HDL-ApoM-S1P (a high density lipoprotein in which apolipoprotein M is impregnated with sphingosine-1-phosphate), and more particularly, to using HDL-ApoM-S1P to prevent, improve, or treat degenerative brain disorders (in particular, Alzheimer's), cognitive disorders, learning disabilities, and memory disorders, and using HDL-ApoM-S1P to improve cognitive ability, learning ability, and memory.

BACKGROUND OF THE INVENTION

The bioactive sphingolipid metabolite, sphingosine-1-phosphate (S1P), is involved in many important cell processes. S1P is produced through the process of phosphorylation of sphingosine by sphingosine kinases (SphKs) and sent out of cells via a carrier such as Spns2 (spinster homolog 2). In innate and adaptive immunity, the action of S1P is mediated by binding to five G protein-coupled receptors, S1P receptors (S1PRs) 1-5. The differential S1P concentration gradient of S1P promotes the escape of lymphocytes from lymphoid organs (Masayo Aoki et al., Sphingosine-1-Phosphate Signaling in Immune Cells and Inflammation: Roles and Therapeutic Potential, Mediators of Inflammation Volume 2016 (2016), 11 pages). In addition, the intracellular action of S1P plays an important role in inflammation by the activation of the transcription factor NF-κB, and it has been reported that S1P mimics the effects of the inflammatory cytokine TNF-α (Wei-Ching Huang et al., Emerging Role of Sphingosine-1-phosphate in Inflammation, Cancer, and Lymphangiogenesis, Biomolecules. 2013 September; 3 (3): 408-434.). Dania Yaghobian et al., said that increased S1P mediates inflammation and fibrosis in tubular injury in diabetic nephropathy (Dania Yaghobian et al., Increased sphingosine 1-phosphate mediates inflammation and fibrosis in tubular injury in diabetic nephropathy, Clinical and Experimental Pharmacology and Physiology (2016) 43, 56-66). It has also been known to induce neuronal death when S1P accumulation produced by sphingosine-kinase2 occurs under S1P-lyase deficiency (Sphingosine-1-phosphate links glycosphingolipid metabolism to neurodegeneration via a calpain-mediated mechanism, Cell Death and Differentiation (2011) 18, 1356-1365).

However, these S1Ps were originally known to have proliferation, differentiation and cell viability activity of cells. As described above, various activities of S1P have been reported according to the specific disease environment (mechanism), and the way of action or effect is reported in the body according to the binding partner that works together in vivo, so much research on S1P is required.

High density lipoprotein (HDL) is known as the major cholesterol carrier in the body. The HDL is one of the major fractions of plasma lipoprotein, which means lipoprotein with specific gravity 1.063-1.210 in ultracentrifugal method. HDL is known to be composed of cholesterol, phospholipids, and apoproteins. ApoAI and ApoAII are known as major proteins in the apoproteins and include ApoC group, ApoE group, and ApoM.

On the other hand, it is known that inflammation contributes to AD pathology based on many toxic inflammatory proteins that are upregulated in the brain of Alzheimer's disease (AD) patients. Douglas Walker and Lih-Fen Lue examined whether inflammation suppression is an effective therapeutic target for treating Alzheimer's disease. However, the drugs were apparently ineffective in clinical trials evaluating the effects of test drugs known to have anti-inflammatory effects on slowing the progression of mental deterioration (Douglas Walker and Lih-Fen Lue, Anti-inflammatory and Immune Therapy for Alzheimer's Disease: Current Status and Future Directions, Curr Neuropharmacol. 2007 December; 5 (4)): 232-243.). Specifically, "Prospective double-blind placebo-controlled trials" is a standard method of determining whether a drug is effective for a particular disease. Many attempts to treat anti-inflammatory agents in AD patients have been performed using this method. As a result of clinical trial taking diclofenac (the diclofenac is used in combination with misoprostol to protect the gastrointestinal tract), an NSAID (nonsteroidal anti-inflammatory drug) in mild to moderate AD patients, there was no significant difference in the index of cognitive decline between the patients taking the drug and the placebo patients after 25 weeks. Small 24-week studies using nimesulide, an NSAID, also showed no significant difference in the rate of cognitive change. In addition, it was not effective in delaying cognitive decline compared to placebo patients in the clinical trial of large-scale for rofecoxib or naproxen for a one-year. In a trial of rofecoxib for 1 year in mild to moderate AD patients, the drug was found to be ineffective. The anti-inflammatory hydroxychloroquine also showed no protective effect in preventing memory degradation in an 18-month experiment. In addition, a trial of prednisone, a strong steroidal anti-inflammatory used at low doses for one year also showed no difference in cognitive decline between the treatment and placebo groups of the drug.

The results of these clinical trials show that simply inhibiting neuroinflammatory phenomena in Alzheimer's disease does not have a significant memory impairment or recovery effect. In other words, there is a considerable mechanistic difference between suppressing (preventing) and treating degenerative brain (nerve) diseases such as Alzheimer's disease. As described above, there have been attempts to be applied to the treatment of degenerative brain (nerve) diseases through the inhibition of neuro-inflammatory, but since these neuro-inflammatory substances do not show a substantial therapeutic effect of the disease, other therapeutic strategies are required for treating degenerative brain (nerve) diseases including Alzheimer's disease.

DETAILED DESCRIPTION OF THE INVENTION

Technical Problem

Therefore, the present inventors, while studying a new strategy for treating effective degenerative brain (nerve)

diseases, confirmed the significant cognitive, learning and memory improvement effect in animal models of Alzheimer's disease through S1P loading in the ApoM region of HDL (high density lipoprotein). In addition, the present invention has been completed after they have confirmed that the increase in HDL-ApoM-S1P in the body can show the cognitive, learning and memory improvement effect even for normal individuals.

Accordingly, an aspect of the present invention is directed to provide a pharmaceutical composition and a pharmaceutical agent comprising the same to prevent or treat degenerative brain disease, comprising a high density lipoprotein (HDL-ApoM-S1P) in which apolipoprotein M is impregnated with sphingosine-1-phosphate as an active ingredient.

Another aspect of the present invention is to provide a pharmaceutical composition and a pharmaceutical agent comprising the same to prevent or treat cognitive disorders, learning disabilities, and memory disorders, comprising a high density lipoprotein (HDL-ApoM-S1P) in which apolipoprotein M is impregnated with sphingosine-1-phosphate as an active ingredient.

Another aspect of the present invention is to provide a pharmaceutical composition and a pharmaceutical agent comprising the same to prevent or treat cognitive disorders, learning disabilities, and memory disorders, consisting of a high density lipoprotein (HDL-ApoM-S1P) in which apolipoprotein M is impregnated with sphingosine-1-phosphate.

Another aspect of the present invention is to provide a pharmaceutical composition and a pharmaceutical agent comprising the same to prevent or treat cognitive disorders, learning disabilities, and memory disorders, consisting essentially of a high density lipoprotein (HDL-ApoM-S1P) in which apolipoprotein M is impregnated with sphingosine-1-phosphate as an active ingredient.

Another aspect of the present invention is to provide a pharmaceutical composition and a pharmaceutical agent comprising the same to improve cognitive ability, learning ability, and memory, comprising a high density lipoprotein (HDL-ApoM-S1P) in which apolipoprotein M is impregnated with sphingosine-1-phosphate as an active ingredient.

Another aspect of the present invention is to provide a pharmaceutical composition and a pharmaceutical agent comprising the same to improve cognitive ability, learning ability, and memory, consisting of a high density lipoprotein (HDL-ApoM-S1P) in which apolipoprotein M is impregnated with sphingosine-1-phosphate.

Another aspect of the present invention is to provide a pharmaceutical composition and a pharmaceutical agent comprising the same to improve cognitive ability, learning ability, and memory, consisting essentially of a high density lipoprotein (HDL-ApoM-S1P) in which apolipoprotein M is impregnated with sphingosine-1-phosphate as an active ingredient.

Still another aspect of the present invention is to provide a use of a high density lipoprotein (HDL-ApoM-S1P) in which apolipoprotein M is impregnated with sphingosine-1-phosphate for preparing a therapeutic agent for degenerative brain disease.

Still another aspect of the present invention is to provide a method for treating degenerative brain disease, the method comprising administering an effective amount of a composition comprising a high density lipoprotein (HDL-ApoM-S1P) in which apolipoprotein M is impregnated with sphingosine-1-phosphate as an active ingredient to an individual in need thereof.

Still another aspect of the present invention is to provide a use of a high density lipoprotein (HDL-ApoM-S1P) in which apolipoprotein M is impregnated with sphingosine-1-phosphate for preparing a therapeutic agent for cognitive disorders, learning disabilities, and memory disorders Still another aspect of the present invention is to provide a method for treating cognitive disorders, learning disabilities, and memory disorders, the method comprising administering an effective amount of a composition comprising a high density lipoprotein (HDL-ApoM-S1P) in which apolipoprotein M is impregnated with sphingosine-1-phosphate as an active ingredient to an individual in need thereof.

Still further aspect of the present invention is to provide a use of a high density lipoprotein (HDL-ApoM-S1P) in which apolipoprotein M is impregnated with sphingosine-1-phosphate for preparing an agent for improving cognitive ability, learning ability, and memory Still further aspect of the present invention is to provide a method for improving cognitive ability, learning ability, and memory, the method comprising administering an effective amount of a composition comprising a high density lipoprotein (HDL-ApoM-S1P) in which apolipoprotein M is impregnated with sphingosine-1-phosphate as an active ingredient to an individual in need thereof.

Technical Solution

An embodiment according to an aspect of the present invention provides a pharmaceutical composition and a pharmaceutical agent comprising the same to prevent or treat degenerative brain disease, comprising a high density lipoprotein (HDL-ApoM-S1P) in which apolipoprotein M is impregnated with sphingosine-1-phosphate as an active ingredient.

An embodiment according to another aspect of the present invention provides a pharmaceutical composition and a pharmaceutical agent comprising the same to prevent or treat cognitive disorders, learning disabilities, and memory disorders, comprising a high density lipoprotein (HDL-ApoM-S1P) in which apolipoprotein M is impregnated with sphingosine-1-phosphate phosphate as an active ingredient.

An embodiment according to another aspect of the present invention provides a pharmaceutical composition and a pharmaceutical agent comprising the same to prevent or treat cognitive disorders, learning disabilities, and memory disorders, consisting of a high density lipoprotein (HDL-ApoM-S1P) in which apolipoprotein M is impregnated with sphingosine-1-phosphate.

An embodiment according to another aspect of the present invention provides a pharmaceutical composition and a pharmaceutical agent comprising the same to prevent or treat cognitive disorders, learning disabilities, and memory disorders, consisting essentially of a high density lipoprotein (HDL-ApoM-S1P) in which apolipoprotein M is impregnated with sphingosine-1-phosphate as an active ingredient.

An embodiment according to another aspect of the present invention provides a pharmaceutical composition and a pharmaceutical agent comprising the same to improve cognitive ability, learning ability, and memory, comprising a high density lipoprotein (HDL-ApoM-S1P) in which apolipoprotein M is impregnated with sphingosine-1-phosphate as an active ingredient.

An embodiment according to still another aspect of the present invention provides a pharmaceutical composition and a pharmaceutical agent comprising the same to improve cognitive ability, learning ability, and memory, consisting of a high density lipoprotein (HDL-ApoM-S1P) in which apolipoprotein M is impregnated with sphingosine-1-phosphate.

An embodiment according to still another aspect of the present invention provides a pharmaceutical composition and a pharmaceutical agent comprising the same to improve cognitive ability, learning ability, and memory, consisting essentially of a high density lipoprotein (HDL-ApoM-S1P) in which apolipoprotein M is impregnated with sphingosine-1-phosphate as an active ingredient.

An embodiment according to still another aspect of the present invention provides a use of a high density lipoprotein (HDL-ApoM-S1P) in which apolipoprotein M is impregnated with sphingosine-1-phosphate for preparing a therapeutic agent for degenerative brain disease.

An embodiment according to still further aspect of the present invention provides a method for treating degenerative brain disease, the method comprising administering an effective amount of a composition comprising a high density lipoprotein (HDL-ApoM-S1P) in which apolipoprotein M is impregnated with sphingosine-1-phosphate as an active ingredient to an individual in need thereof.

An embodiment according to still further aspect of the present invention provides a use of a high density lipoprotein (HDL-ApoM-S1P) in which apolipoprotein M is impregnated with sphingosine-1-phosphate for preparing a therapeutic agent for cognitive disorders, learning disabilities, and memory disorders.

An embodiment according to still further aspect of the present invention provides a method for treating cognitive disorders, learning disabilities, and memory disorders, the method comprising administering an effective amount of a composition comprising a high density lipoprotein (HDL-ApoM-S1P) in which apolipoprotein M is impregnated with sphingosine-1-phosphate as an active ingredient to an individual in need thereof.

An embodiment according to still further aspect of the present invention provides a use of a high density lipoprotein (HDL-ApoM-S1P) in which apolipoprotein M is impregnated with sphingosine-1-phosphate for preparing an agent for improving cognitive ability, learning ability, and memory An embodiment according to still further aspect of the present invention provides a method for improving cognitive ability, learning ability, and memory, the method comprising administering an effective amount of a composition comprising a high density lipoprotein (HDL-ApoM-S1P) in which apolipoprotein M is impregnated with sphingosine-1-phosphate as an active ingredient to an individual in need thereof.

Hereinafter, the present invention will be described in detail.

The term 'a high density lipoprotein (HDL-ApoM-S1P) in which apolipoprotein M is impregnated with sphingosine-1-phosphate' may be represented as 'HDL-ApoM-S1P', and the HDL (i.e., HDL-ApoM-S1P) provided in the present invention is characterized in that ApoM is impregnated with S1P. HDL-ApoM-S1P administered into the body has a specific relationship with ApoM and is characterized in that it exhibits a specific improvement and a therapeutic effect for degenerative brain disease (especially Alzheimer's disease), cognition ability, memory, or learning ability in animals. When HDL and S1P are mixed, the major plasma apolipoprotein to which S1P physically binds is known to be ApoM, the majority of which is contained in HDL.

In the present invention, the term 'loading' refers to include containing (comprising), linking, binding or conjugate.

In the present invention, the degenerative brain disease may be preferably selected from the group consisting of Alzheimer's disease, Parkinson's disease, Huntington's chorea, Pick's disease, and Creutzfeld-Jacob's disease.

In the present invention, the term of Alzheimer's disease is a degenerative brain disease, and is a representative disease causing dementia mainly in the elderly. The disease is characterized by the accumulation of β-amyloid peptides (A13) and the formation of paired helical filaments (PHFs), which are mostly composed of hyperphosphorylated tau proteins. Nerve cells are known to be killed by extracellular beta amyloid deposition and intracellular hyperphosphorylated tau proteins throughout the brain, resulting in progressive memory disorders, cognitive deficits, and personality changes. Alzheimer's disease of the present invention refers to include dementia of Alzheimer's type.

In the present invention, the term of cognitive disorders shows an abnormality in the cognitive ability regarding the way of acquiring and using knowledge. The cognitive ability includes the mental ability, such as knowledge, understanding, thinking, problem solving, criticality and creativity.

In addition, learning disabilities exhibit remarkable difficulty in learning functions such as listening, speaking, attention, perception, memory, problem solving, and academic achievement areas such as reading, writing, and mathematics.

In addition, memory disorder is a condition in which it is difficult or impossible to remember a newly learned fact, to remember the name of an object or person, or to recall past experiences.

Such cognitive disorder, memory (ability) disorder, or learning disability may be caused by various causes and environments, and the cause is not particularly limited in the present invention. For example, it may be due to aging, Alzheimer's disease, dementia, mild cognitive impairment, cognitive deficit and attention deficit.

When the present inventors performed S1P loading on the ApoM region of high density lipoprotein (HDL) in Alzheimer's disease individuals (animals), or, in other word, when a HDL (HDL-ApoM-S1P) in which ApoM is impregnated with S1P is administrated, not only does it alleviates neuroinflammation but also significantly exhibits improvement effects of cognitive disorder, learning disability, and memory disorder. Amyloid beta and tau deposits were significantly reduced. It was confirmed that the effect of the HDL-ApoM-S1P of the present invention is ApoM-dependent with a special relation to ApoM. In addition, the present inventors confirmed that increased HDL-ApoM-S1P in the body also has an excellent effect of improving the cognitive, learning, and memory abilities of non-disabled individuals. The novel uses of HDL-ApoM-S1P for degenerative brain diseases (particularly, Alzheimer's disease), cognition, learning and memory are for the first time disclosed in the present invention.

Therefore, the present invention provides a pharmaceutical composition to prevent, improve, and/or treat brain disorders (in particular, Alzheimer's), cognitive disorders, learning disabilities, and memory disorders, comprising a high density lipoprotein (HDL-ApoM-S1P) in which apolipoprotein M is impregnated with sphingosine-1-phosphate as an active ingredient.

In addition, the present invention provides a pharmaceutical composition to improve cognitive ability, learning ability, and memory, comprising a high density lipoprotein (HDL-ApoM-S1P) in which apolipoprotein M is impregnated with sphingosine-1-phosphate as an active ingredient.

The present invention is also to provide a pharmaceutical composition to prevent, improve, and/or treat brain disorders (in particular, Alzheimer's), cognitive disorders, learning disabilities, and memory disorders, consisting of a high density lipoprotein (HDL-ApoM-S1P) in which apolipoprotein M is impregnated with sphingosine-1-phosphate.

The present invention provides a pharmaceutical composition to improve cognitive ability, learning ability, and memory, consisting of a high density lipoprotein (HDL-ApoM-S1P) in which apolipoprotein M is impregnated with sphingosine-1-phosphate.

In addition, the present invention is to provide a pharmaceutical composition to prevent, improve, and/or treat brain disorders (in particular, Alzheimer's), cognitive disorders, learning disabilities, and memory disorders, consisting essentially of a high density lipoprotein (HDL-ApoM-S1P) in which apolipoprotein M is impregnated with sphingosine-1-phosphate as an active ingredient.

The present invention also provides a pharmaceutical composition to improve cognitive ability, learning ability, and memory, consisting essentially of a high density lipoprotein (HDL-ApoM-S1P) in which apolipoprotein M is impregnated with sphingosine-1-phosphate as an active ingredient.

In the present invention, 'Sphingosine-1-Phosphate (S1P)' is a compound represented by the following <Formula 1>. S1P in plasma is known to be produced and supplied mainly by platelets, erythrocytes, and endothelial cells. Mast cells and macrophages are also known to produce S1P. The sphingosine-1-phosphate may be extracted and used from blood and tissue samples separated (collected) from animals according to methods known in the art. It can be commercially purchased or prepared by chemical synthesis methods known in the art.

<Formula 1>

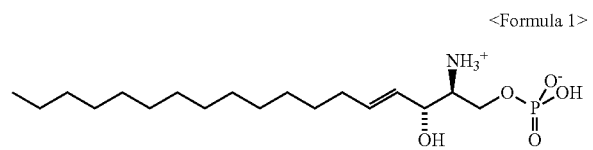 [SMILES: CCCCCCCCCCCCC/C=C/[C@@H](O)[C@@H]([NH3+])COP(=O)([O-])O]

In the present invention, 'high density lipoprotein (HDL)' is one of the major fractions of plasma lipoprotein, which refers to lipoprotein with specific gravity 1.063-1.210 in ultracentrifugal method. High-density lipoprotein is about 17% cholesterol and about 22% phospholipid in about $2\lambda10^5$ molecular weight. The protein part accounts for about 50% and the main apoprotein is ApoA. Therefore, ApoAI and ApoAII are the main proteins and include ApoC group, ApoE group, and ApoM. The HDL of the present invention can be used to separate those present in the natural according to methods known in the art. For example, it may be used by extracting (purifying) from a blood sample separated (collected) from an animal through a method such as centrifugation. It may also be commercially purchased or prepared by a synthetic HDL (reconstituted HDL) manufacturing method or a HDL-like nanostructure manufacturing method known in the art. Reference may be made to BRICARELLO et al., ACS NANO 5 (1), 42-57 (2010), or a method for preparing nanoparticles of high density lipoprotein presented in Republic of Korea Patent Registration 10-1132626 and Republic of Korea Patent Registration 10-0588241. In the present invention, HDL is characterized in that it comprises essentially ApoM, and it is possible to use both native HDL and HDL-like nanostructures including ApoM.

As used herein, the term of native HDL refers to HDL which is generally found in a natural state, i.e., in vivo in an animal. As described above, the HDL is one of the major fractions of plasma lipoprotein, which refers to lipoprotein with specific gravity 1.063-1.210.

In the present invention, the term 'HDL-like nanostructure' or 'HDL nanoparticles' refers to reconstituted and synthetic nanostructures similar in size, composition, and properties (e.g., lipid transport properties in the body, specific gravity (density), etc.) to native HDL. Reconstituted HDL-like nanostructures are generally 5-15 nm in diameter.

The HDL-like nanostructures may be in the form of nanodisks of 5-15 nm in diameter, more preferably 5-8 nm in diameter. In addition, the HDL-like nanostructures of the present invention may be in the form of nanospheres of 5-15 nm in diameter, more preferably 10-15 nm in diameter. The HDL-like nanostructures can be reconstituted by adding phospholipids and apolipoproteins and by mixing and/or incubating under appropriate reaction conditions (e.g. with the use of suitable surfactants and solvents). Reference can be made to the following literature: BRICARELLO et al., ACS NANO 5 (1), 42-57 (2010); Republic of Korea Patent Registration 10-1132626; Republic of Korea Patent Registration 10-0588241. In addition, the HDL-like nanostructures may further include cholesterol or cholesterol derivatives.

The phospholipid component of the reconstituted HDL-like nanostructures may be using only one type of phospholipid or a mixture of two or more different types. Specifically, the type of the phospholipid is not particularly limited as long as it is known in the art for preparing HDL, but may be one or more selected from the group consisting of egg yolk phosphatidylcholine, soy phosphatidylcholine, ether phospholipid, small alkyl chain phospholipid, dipalmitoylphosphatidylcholine, dimyristoylphosphatidylcholine, distearoylphosphatidylcholine, 1-myristoyl-2-palmitoyl phosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleylphosphatidylcholine, dioleoylphosphatidylethanolamine, dilauylphosphatidylglycerol phosphatidylcholine, phosphatidylserine, phosphatidylethanolamine, phosphatidyl inositol, sphingomyelin sphingolipid, phosphatidylglycerol, diphosphatidylglycerol, dimyristoylphosphatidylglycerol, dipalmitoylphosphatidylglycerol, distearoylphosphatidylglycerol, dioleylphosphatidylglycerol, dimyristoylphosphatidic acid, dipalmitoylphosphatidyl acid, dimyristoylphosphatidylethanolamine, dipalmitoylphosphatidylethanolamine, dimyristoylphosphatidylserine, dipalmitoylphosphatidylserine and dilaurylphosphatidylcholine.

The apolipoprotein of the reconstituted HDL-like nanostructure is characterized in that ApoM is necessarily used in the present invention, and may further include a known HDL apolipoprotein component. For example, one or more selected from ApoA-I, ApoA-II, ApoA-IV, ApoC-I, ApoC-II, ApoC-Ill, ApoE and ApoM may be used, but is not limited thereto.

If the apolipoprotein is known in the art, the specific amino acid sequence is not particularly limited. For example, ApoM as a human apolipoprotein may be used as NCBI Reference Sequence: NP_061974.2, NP_001243098.1, ApoA-I may be used as NCBI Reference Sequence (accession no): NP_001304947.1, NP_001304950.1, ApoA-II may be used as NCBI Reference Sequence (accession no): NP_001634.1, ApoA-IV may be used as NCBI Reference Sequence (accession no): P06727.3, ApoC-I may be used as NCBI Reference Sequence (accession no): NP_001307995.1, ApoC-II may be used as NCBI Reference Sequence (accession no):

P02655.1, ApoC-III may be used as NCBI Reference Sequence (accession no): P02656.1, and ApoE may be used as NCBI Reference Sequence (accession no): P02649.1, but is not limited thereto.

The method for obtaining 'HDL-ApoM-S1P' of the present invention or a method for impregnating sphingosine-1-phosphate on high density lipoproteins is known in the art, and there is no particular restriction on the method of preparing the 'HDL-ApoM-S1P' of the present invention. When HDL and S1P are mixed, the major plasma apolipoprotein to which S1P physically binds is known to be apoprotein M (ApoM), the majority of which is contained in HDL.

In one example, native HDL or reconstituted HDL-like nanostructures containing ApoM can be directly mixed and incubated with S1P (especially, under conditions capable of forming ApoM-S1P complexes).

In one example, a native HDL or reconstituted HDL-like nanostructure containing ApoM can be co-cultured with cells known as a source of S1P (one or more than one cell mixture) in the body of the animal. Cells known to be capable of producing S1P include erythrocytes, platelets, endothelial cells, mast cells or macrophage. The co-culture may make a culture environment in which the release of S1P is increased (activated) according to each cell type, and such culture conditions are not particularly limited as long as they are known in the art.

As a specific example, it is known that S1P is released from erythrocytes when native HDL is incubated with erythrocytes (Constantin Bode et al., Erythrocytes Serve as a Reservoir for Cellular and Extracellular Sphingosine 1-Phosphate, Journal of Cellular Biochemistry 109:1232-1243 (2010)), and the S1P released from erythrocytes is impregnated in native HDL, where ApoM of the HDL is known to the major binding site. In addition, since the specific apolipoproteins that induce release of S1P from erythrocytes in native HDL are known to be ApoC-I and ApoCII in Constantin Bode et al., (2010), the reconstituted HDL-like nanostructures constructed with ApoC-I and ApoCII proteins can also induce S1P release from erythrocytes when co-cultured with erythrocytes and can be impregnated with the constructs. As a method of increasing the release of S1P from erythrocytes in co-culture of HDL and erythrocytes, for example, a method of pre-incubating sphingosine in erythrocytes before co-culture with HDL may be used.

As another example, since S1P accumulated in platelets is known to promote the release of S1P from platelets by treating $Ca^{2+}$ (Nobuyoshi Kobayashi, Sphingosine 1-phosphate is released from the cytosol of rat platelets in a carrier-mediated manner, The Journal of Lipid Research, 47, 614-621.), $Ca^{2+}$ may be treated together in co-culture of platelets and HDL (Native HDL or reconstituted HDL-like nanostructures).

Most preferably, the method of preparing HDL-ApoM-S1P in the present invention may be a method of co-culture of HDL containing ApoM with erythrocytes, and it may be more preferable to include the pre-incubation of sphingosine in erythrocytes to increase the efficiency of S1P release from erythrocytes in the co-culture.

The HDL-ApoM-S1P of the present invention is most preferably prepared by a manufacturing method comprising the following steps (a) to (d), and it may be provided to an individual in need of treating brain disorders (in particular, Alzheimer's), cognitive disorders, learning disabilities, and memory disorders (a) separating blood collected from the individual into plasma and blood cell fractions;
(b) treating sphingosin to the blood cell fraction obtained in the step (a);
(c) mixing the blood cell fraction of the step (b) and the plasma fraction of the step (a); and
(d) separating the plasma fraction from the mixture of the step (c).

In step (a), a blood sample isolated from the individual is separated into a plasma fraction and a blood cell fraction.

The plasma fraction of the step (a) includes HDL-ApoM (HDL containing ApoM), and the blood cell fraction is characterized in that it comprises erythrocytes. As long as the plasma fraction contains HDL-ApoM and the blood cell fraction contains erythrocytes, the difference in the remaining blood components in each fraction may be removed beforehand or include additional components as would be appreciated by those skilled in the art.

The method of fractionating blood samples into plasma and blood cells is well known in the art and the method may be, for example, by centrifugation.

In step (b), the blood cell fraction obtained in the step (a) is cultured by treating sphingosin.

The erythrocytes contained in the blood cell fraction include sphingosine kinases (Sphk1 and Sphk2), and the sphingosine treated in the blood cell fraction is phosphorylated by the sphingosine kinases to produce and release a large amount of S1P (from erythrocytes). The treatment concentration of sphingosine, the culture temperature, and the time in the culture can be appropriately changed according to the release amount and release rate of S1P intended by those skilled in the art, and are not particularly limited.

In step (c), the blood cell fraction of the step (b) and the plasma fraction of the step (a) are mixed and reacted (cultured).

After completion of step (b), the blood cell fraction contains a large amount of S1P, and the HDL in the plasma by the mixing impregnates the S1P, and in particular, a large amount of S1P binds to ApoM, a major binding partner on HDL. Conditions such as temperature and time of the reaction (culture) can be appropriately changed depending on the degree of productivity (efficiency) of HDL-ApoM-S1P production intended by those skilled in the art, and is not particularly limited.

In step (d), the plasma fraction is separated again from the reaction mixture in the step (c).

The method of fractionating (separating) the plasma in step (d) is as described above in the step (a). The plasma fraction prepared in the step (d) is enriched with HDL-ApoM-S1P.

The plasma fraction prepared in the step (d) is preferably administered to the same individual from which the blood sample is separated in the step (a). When the HDL-ApoM-S1P of the present invention is prepared in the same manner as described above and provided to the individual in the plasma fraction of the step (d), there is an advantage that the occurrence of other side effects (for example, immune or blood coagulation reactions between non-identical individuals) is substantially or significantly reduced because the plasma fraction provided in step (d) is not heterogeneous with the original blood component of the individual.

In addition, the HDL-ApoM-S1P manufacturing method may further comprise (e) purifying (or concentrating) HDL-ApoM-S1P from the plasma fraction of the step (d), and it is possible to provide a high concentration of HDL-ApoM-S1P as an active ingredient through the purification.

The purification is not particularly limited as long as it is the separation or purification method of blood components known in the art, but may be, for example, centrifugation or chromatography (for example, liquid chromatography).

The pharmaceutical composition may further include a substance known in the art to have a therapeutic effect on degenerative brain diseases (particularly Alzheimer's disease) or dementia in addition to the active ingredient of the present invention. As examples, tacrine, donepezil, rivastigmine, galantamine, and memantine are included, but are not limited to.

The pharmaceutical composition according to the present invention may comprise HDL-ApoM-S1P alone or may further comprise one or more pharmaceutically acceptable carriers, excipients or diluents. Pharmaceutically acceptable carriers may further include, for example, carriers for oral administration or carriers for parenteral administration. Carriers for oral administration may include lactose, starch, cellulose derivatives, magnesium stearate, and stearic acid. In addition, carriers for parenteral administration may include water, suitable oils, saline, aqueous glucose and glycols, and may further include stabilizers and preservatives. Suitable stabilizers include antioxidants such as sodium hydrogen sulfite, sodium sulfite or ascorbic acid. Suitable preservatives include benzalkonium chloride, methyl- or propyl-parabens and chloro butanol. Other pharmaceutically acceptable carriers may be referred to those described in the following reference (Remington's Pharmaceutical Sciences, 19th ed., Mack Publishing Company, Easton, Pa., 1995).

As used herein, "pharmaceutically acceptable" is physiologically acceptable and refers to a non-toxic composition that, when administered to humans, does not inhibit the action of the active ingredient and usually does not cause an allergic reaction such as gastrointestinal disorders, or dizziness. The composition of the present invention may be variously formulated according to the route of administration by a method known in the art together with the pharmaceutically acceptable carrier. The routes of administration may be administered orally or parenterally, but are not limited to.

The pharmaceutical composition of the present invention can be administered to any mammal in any way, including humans. For example, it can be administered orally or parenterally. Parenteral administration methods include intravenous, intramuscular, intra-arterial, intramedullary, intradural, intracardiac, transdermal, subcutaneous, intraperitoneal, intranasal, intestinal, topical, sublingual or rectal administration, but are not limited to. Preferably the pharmaceutical composition of the present invention may be administered intravascularly (intravenously or intra-arterially).

The pharmaceutical composition of the present invention may be formulated into an agent for oral or parenteral administration according to the route of administration as described above. In addition, the pharmaceutical compositions of the present invention may be formulated using methods known in the art to provide rapid, sustained or delayed release of the active ingredient after administration to a mammal.

In the case of the agents for oral administration, the compositions of the present invention are formulated using methods known in the art as powders, granules, tablets, pills, dragees, capsules, solutions, gels, syrups, slurries, and suspension. For example, an agent for oral administration can be obtained by tablets or dragees by combining the active ingredients with solid excipients and then grinding them, adding suitable auxiliaries and processing them into granule mixtures. Examples of the suitable excipients may include sugars including lactose, dextrose, sucrose, sorbitol, mannitol, xylitol, erythritol and maltitol, starches including corn starch, wheat starch, rice starch and potato starch, celluloses including cellulose, methyl cellulose, sodium carboxymethylcellulose, and hydroxypropylmethyl-cellulose, and fillers such as gelatin and polyvinylpyrrolidone. In addition, cross-linked polyvinylpyrrolidone, agar, alginic acid or sodium alginate may optionally be added as a disintegrant. Furthermore, the pharmaceutical composition of the present invention may further include an anticoagulant, a lubricant, a humectant, a perfume, an emulsifier, and a preservative.

The agents for parenteral administration may be formulated by methods known in the art in the form of injections, creams, lotions, external ointments, oils, humectants, gels, aerosols and nasal inhalants. These formulations are described in a reference generally known in all pharmaceutical chemistries (Remington's Pharmaceutical Science, 15th Edition, 1975. Mack Publishing Company, Easton, Pa. 18042, Chapter 87: Blaug, Seymour). Examples of suitable carriers for injections may include, but are not limited to, solvents or dispersion media including water, ethanol, mixtures of polyols (e.g., glycerol, propylene glycol, liquid polyethylene glycols, etc.) and/or vegetable oils. More preferably, the suitable carriers may include phosphate buffered saline (PBS) containing Hanks solution, Ringer's solution triethanol amine or isotonic solutions such as sterile water for injection, 10% ethanol, 40% propylene glycol and 5% dextrose. In order to protect the injection from microbial contamination, various antibacterial and antifungal agents such as parabens, chlorobutanol, phenol, sorbic acid, and thimerosal may be further included. In addition, the injection may in most cases further include an isotonic agent such as sugar or sodium chloride.

The pharmaceutical composition of the present invention may be administered to a patient in a single dose, and may be administered by a fractionated treatment protocol in which multiple doses are administered for a long time. The pharmaceutically effective amount refers to an amount that exhibits a higher response than the negative control, and preferably, a sufficient amount used for improving, treating, or preventing degenerative brain disease (especially, Alzheimer's disease), cognitive disorders, learning disabilities, or memory disorders. An effective amount of HDL-ApoM-S1P according to the present invention may be 0.001 to 1000 mg/day/kg body weight, more preferably 0.01 to 100 mg/day/kg, but is not limited thereto. However, with respect to the pharmaceutically effective amount, a person skilled in the art may determine the effective dosage (effective amount), frequency of administration, route of administration of the composition according to the present invention by appropriate consideration of various factors such as age, weight, health condition, sex, diet and excretion rate of the individual in need of administration to have the effect of preventing or treating degenerative brain disease (especially Alzheimer's disease), cognitive impairment, learning disability or memory impairment The present invention also provides a pharmaceutical agent for preventing or treating degenerative brain disease, cognitive disorders, learning disabilities, or memory disorders comprising the pharmaceutical composition. In another aspect, the present invention provides a pharmaceutical preparation for improving cognitive ability, learning ability, and memory comprising the pharmaceutical composition.

The pharmaceutical agent of the present invention comprises the pharmaceutical composition of the present invention described above. The pharmaceutical agent of the present invention is not particularly limited in the formulation as long as it shows the effect according to the present invention.

The pharmaceutical agent of the present invention may be formulated in a suitable form according to the administration method and route of administration. The pharmaceutically acceptable carriers that can be included in routes of administration, methods of administration, specific formulation methods and the formulation in the present invention are the same as described above in the pharmaceutical composition, and may be referred to the following literature (Remington's Pharmaceutical Sciences, 19th ed., Mack Publishing Company, Easton, Pa., 1995). Preferably the agent of the invention may be an injection. The injection of the invention may preferably be administered intravascularly (intravenously or intra-arterally). Suitable carriers when formulated as injections include pharmaceutically acceptable isotonic agents, solubilizers, analgesics, stabilizers, buffers, and preservatives known in the art. The term "pharmaceutically acceptable" is physiologically acceptable and refers to no allergic or allergic-like reactions such as common gastrointestinal disorders, or dizziness when administered to humans or animals. Suitable stabilizers include sodium bisulfite, sodium sulfite and ascorbic acid, and preservatives include, but are not limited to, benzalkonium chloride, methyl or propyl-paraben and chlorobutanol.

Preferred dosages of the pharmaceutical agents of the present invention may appropriately vary depending on various factors such as the disease, its severity, the age, weight, health status, sex of the patient, the route of administration, and the duration of treatment. Since the bioavailability of the pharmaceutically active ingredient (individual) is individual, it may be desirable that the blood concentration of each drug is confirmed by an assay based on a monoclonal antibody known in the art at the beginning of the administration of the pharmaceutical agent of the present invention.

Specific examples of the treatment or the preventive indications of the pharmaceutical agents of the present invention are the same as the specific examples of the treatment or the preventive indications of the pharmaceutical composition of the present invention described above.

The present invention provides a use of a high density lipoprotein (HDL-ApoM-S1P) in which apolipoprotein M is impregnated with sphingosine-1-phosphate for preparing a therapeutic agent for degenerative brain disease.

The present invention provides a method for treating degenerative brain disease, the method comprising administering an effective amount of a composition comprising a high density lipoprotein (HDL-ApoM-S1P) in which apolipoprotein M is impregnated with sphingosine-1-phosphate as an active ingredient to an individual in need thereof.

The present invention provides a use of a high density lipoprotein (HDL-ApoM-S1P) in which apolipoprotein M is impregnated with sphingosine-1-phosphate for preparing a therapeutic agent for cognitive disorders, learning disabilities, and memory disorders.

The present invention provides a method for treating cognitive disorders, learning disabilities, and memory disorders, the method comprising administering an effective amount of a composition comprising a high density lipoprotein (HDL-ApoM-S1P) in which apolipoprotein M is impregnated with sphingosine-1-phosphate as an active ingredient to an individual in need thereof.

The present invention provides a use of a high density lipoprotein (HDL-ApoM-S1P) in which apolipoprotein M is impregnated with sphingosine-1-phosphate for preparing an agent for improving cognitive ability, learning ability, and memory.

The present invention provides a method for improving cognitive ability, learning ability, and memory, the method comprising administering an effective amount of a composition comprising a high density lipoprotein (HDL-ApoM-S1P) in which apolipoprotein M is impregnated with sphingosine-1-phosphate as an active ingredient to an individual in need thereof.

The term 'effective amount' of the present invention, when administered to an individual, refers to an amount indicating the improvement, treatment, prevention, detection, and diagnosis of degenerative brain disease, cognitive disorders, learning disabilities, and memory disorders, or the inhibition or decreased effect of degenerative brain disease, cognitive disorders, learning disabilities, and memory disorders. The 'individual' may be an animal, preferably an animal including a mammal, especially a human, and may be a cell, tissue, or organ derived from the animal. The individual may be a patient in need of the effect.

The term 'treatment' of the present invention refers generically to the improvement of degenerative brain disease, cognitive disorders, learning disabilities, and memory disorders or symptoms of degenerative brain disease, cognitive disorders, learning disabilities, and memory disorders. This may include treating, substantially preventing, improving the condition, and alleviating, treating or preventing one or most of the symptoms resulting from degenerative brain disease, cognitive disorders, learning disabilities, and memory disorders, but is not limited to.

The term 'comprising' of the present invention is used in the same way as 'containing' or 'characteristic', and does not exclude any additional component elements or methods that are not mentioned in the composition or method. The term 'consisting of' refers to additional elements, steps or components, unless otherwise noted. The term "essentially consisting of" means within the scope of the composition or method, including the component elements or steps described and any component elements or steps which do not substantially affect their basic properties.

Advantageous Effect

The HDL-ApoM-S1P according to the present invention not only alleviates neuroinflammation but also significantly exhibits improvement effects of cognitive disorder, learning disability, and memory disorder with respect to individuals suffering from degenerative brain disorders (in particular, Alzheimer's), and exhibits an effect of greatly reducing amyloid beta and tau deposition. Moreover, increased HDL-ApoM-S1P in the body also has an excellent effect of improving the cognitive, learning, and memory abilities of non-disabled individuals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5a and 5b show the results of the Tau deposition in the APP/PS1 mice (an animal model of the Alzheimer's disease), APP/PS1 mice subjected to HDL-ApoM-S1P loading, APP/PS1 mice injected with S1P and APP/PS1 mice injected with ApoM using AT8 staining, which show Microscopic images thereof (FIG. 5a) and quantitative results (FIG. 5b).

FIGS. 6a and 6b show the results of the activity of microglia in the WT (normal control mouse), APP/PS1 mice (an animal model of the Alzheimer's disease), APP/PS1 mice subjected to HDL-ApoM-S1P loading, APP/PS1 mice injected with S1P and APP/PS1 mice injected with ApoM using Iba1 staining, which show Microscopic images thereof (FIG. 6a) and quantitative results (FIG. 6b).

FIGS. 7a and 7b show the results of the activity of astrocytes in the WT (normal control mouse), APP/PS1 mice (an animal model of the Alzheimer's disease), APP/PS1 mice subjected to HDL-ApoM-S1P loading, APP/PS1 mice injected with S1P and APP/PS1 mice injected with ApoM using GFAP staining, which show Microscopic images thereof (FIG. 7a) and quantitative results (FIG. 7b).

FIGS. 13a and 13b show the results of the Tau deposition in APP/PS1 mice and APP/PS1/ApoM tg mice using AT8 staining, which show Microscopic images thereof (FIG. 13a) and quantitative results (FIG. 13b).

FIGS. 14a and 14b show the results of the activity of microglia in the WT (Wild Type, normal control mice), ApoM tg (normal mice overexpressing ApoM), APP/PS1 (an animal model of the Alzheimer's disease) and APP/PS1/ApoM tg mice using Iba1 staining, which show Microscopic images thereof (FIG. 14a) and quantitative results (FIG. 14b).

FIGS. 15a and 15b show the results of the activity of astrocytes in the WT (Wild Type, normal control mice), ApoM tg (normal mice overexpressing ApoM), APP/PS1 (an animal model of the Alzheimer's disease) and APP/PS1/ApoM tg mice using GFAP staining, which show Microscopic images thereof (FIG. 15a) and quantitative results (FIG. 15b).

MODE FOR CARRYING OUT INVENTION

Hereinafter, the present invention will be described in detail.

However, the following examples are illustrative of the present invention, and the present invention is not limited to the following examples.

Experiment Method

1) A Mouse Model of the Alzheimer's Disease

Figure 10:
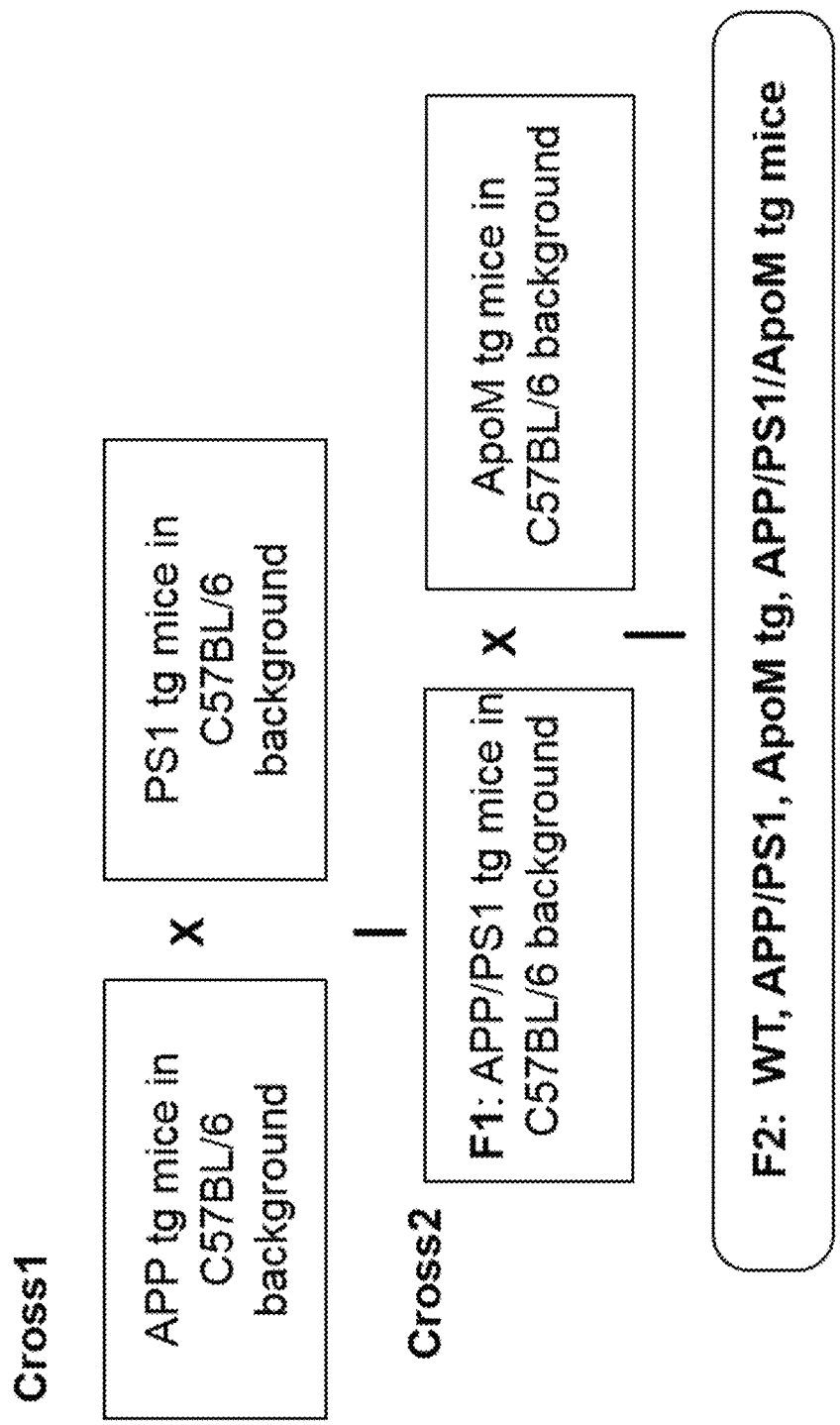
FIG. 10 shows a schematic diagram showing a process of producing APP/PS1/ApoM tg mice by crossing APP/PS1 mice and ApoM tg mice (HDL-ApoM-S1P overexpressing mice) to genetically elevate lowered HDL-ApoM-S1P in an animal model of the Alzheimer's disease (APP/PS1).

Transgenic mice overexpressing hAPP695swe (APPswe) and presenilin-1M146V (PS1) mutations were used as mouse models of the Alzheimer's disease. These are mouse lines produced by GlaxoSmithKline (Harlow, UK) with the standard technology for C57BL background (Charles River, UK), which double heterozygote mutant mice (APP/PS1 tg mice) were produced by backcrossing APPswe mice with pure C57BL/6 backgrounds and crossing PS1 mice In addition, the APP/PS1 tg mice were crossed with ApoM tg mice in the same manner to prepare triple mutant mice (APP/PS1/ApoM tg mice) in which APP/PS1 tg mice overexpress ApoM, and a manufacturing process thereof is shown in FIG. 10.

2) A HDL-ApoM-S1P Loading Protocol and the Treatment Method of Test Materials

After collecting blood from mice, the obtained blood was separated into erythrocytes and plasma by centrifugation. The separated erythrocytes are reacted with 10 uM sphingosine at 37° C. for 1 hour, and then reacted for 1 hour at 37° C. after mixing again with the separated plasma. After completion of the reaction, erythrocytes and plasma were separated by centrifugation, and only the plasma was collected again. The plasma thus obtained was loaded with S1P in HDL (HDL-ApoM-S1P loading), which was illustrated in FIG. 1.

The plasma solution thus obtained was intravenously injected 25 μl into mice twice a week for 4 weeks (total 8 times) according to the experimental outline shown in FIG.

2. As a control group, 3 μM S1P (Avanti) and 50 mM ApoM (Mybiosource, SEQ ID NO: 1) were injected intravenously with 25 μl in mice twice a week for 4 weeks (eight times in total).

3) Protocol of Blood Collection and Plasma Separation

To collect blood from mouse models (APP/PS1 tg mice or APP/PS1/ApoM tg mice) and normal control mice (WT), the mice were anesthetized first, and 500 μl to 700 μl of blood were collected in heparin tubes (BD Falcon) by cardiac drawing. Each blood sample was then centrifuged at 1,200 rpm for 5 minutes to separate plasma from the supernatant. This plasma sample was stored at −80° C. before being used for analysis.

4) Protocol of High Density Lipoprotein (HDL) Fractionation in Plasma

60 μl of plasma sample was placed in the ultrafast centrifuge tube, and then the same amount of PBS (Gibco) solution was added to form a layer on the plasma. A high speed centrifuge (HITACHI cp100wx Centrifuge P70AT rotor) was used to centrifuge at 70,000 rpm for 3 hours at 4° C. 60 μl of the lower layer of the sample separated into two layers was transferred into a new ultra-centrifuge tube. The same amount of NaBr (Sigma-Aldrich) solution (density=1.12 g/ml) was added, mixed about 5 times with a pipette, and then again centrifuged at 70,000 rpm for 18 hours at 4° C. 60 μl of the lower layer HDL of the sample separated into two layers was transferred to a new tube and the sample was stored at −80° C. before being used for analysis.

5) S1P (Sphingosine-1-phosphate) Measurement

Extraction and quantification of S1P was performed in the following manner. 150 μl dichloromethane and methanol respectively, 100 μl dichloromethane and 10% NaHCl in the mouse plasma or HDL fractionated therefrom were added, mixed and centrifuged for 1 minute. 100 μl of the lower layer lipid of the sample separated into two layers was transferred to a new tube and dried using a speed vacuum (5000 rpm, at 50° C.). The dried lipid extract was resuspended in 25 μl of 0.2% Igepal CA-630 (Sigma-Aldrich), and the concentration level of each lipid was quantified by the UPLC system using the column ACQUITY BEH Shield RP18 1.7 μm 2.1×50 mm (186002853) and 0.1% of $NH_4OH$.

6) ApoM (Apolipoprotein M) Measurement

Using a commercial ELISA kit (CUSABIO Human ApoM ELISA Kit and Mouse ApoM ELISA Kit), the amount of apolipoprotein M (ApoM) contained in the mouse plasma or HDL fractionated therefrom was quantified according to the manufacturer's protocol. As a standard curve, purified Apolipoprotein M standard was used.

7) Immunofluorescence

After fixing the cerebral (especially cortex) and hippocampus of mice with 4% paraformaldehyde, the immobilized tissues were incubated with 0.5% thioflavin S (Sigma-Aldrich) or anti-20G10 against Aβ42 (mouse, 1:1000), anti-G30 against Aβ40 (rabbit, 1:1000), anti-lba-1 (rabbit, 1:500, Wako), and anti-GFAP (rabbit, 1:500, DAKO), respectively. For visualization, they were incubated with Alexa Fluor 488-conjugated secondary antibody. The sites were analyzed using a laser scanning confocal microscope or Olympus BX51 microscope equipped with Fluoview SV1000 imaging software (Olympus FV1000, Japan). Metamorph software (Molecular Devices) was used to quantify the percentage of area of stained area to area of total tissue.

8) Behavior Test

In order to identify potential effects on learning and memory, Morris water maze (MWM) and fear conditioning experiments were performed according to known methods. As an underwater maze for MWM, a white tank (1.0 m radius, 30 cm height) filled with 20 cm deep water (22-24° C.) was used. A hidden Plexiglas platform (10 cm diameter; 6-8 mm below the surface of the water) was placed in a fixed position during training. MWM trained the mice 4 times a day for 10 days, removed the platform on day 11, and performed a probe trial. Fear conditioning on the first day put the mouse in the conditioning chamber and gave sound stimulation (10 kHz, 70 dB) and electrical stimulation (0.3 mA, 1 s). On the second day, the memory of the room was confirmed without stimulation in the same conditioning chamber as on the first day. On the third day, the memory test of fear was performed when only the sound stimulation was given in the other conditioning chamber. All experiments were recorded using a charge-coupled device (CCD) camera with video monitor and computer. Tests were performed using Image J software, and all equipment used was made from O'Hara & Company (Tokyo, Japan).

Figure 2:
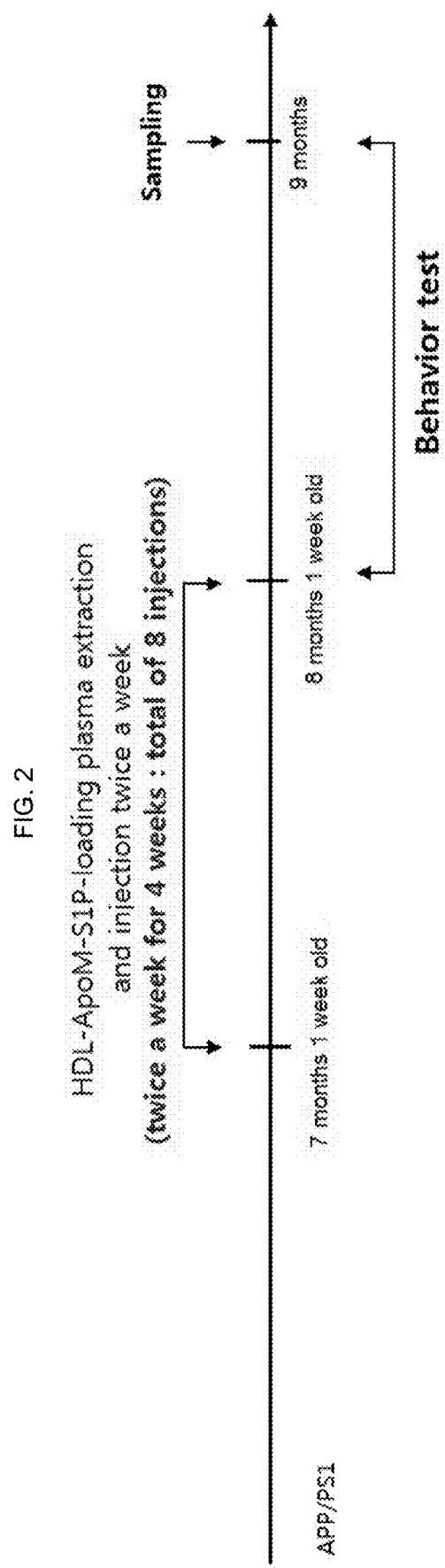
FIG. 2 shows the experimental schedule for confirming the therapeutic effect by the 'HDL-ApoM-S1P loading' in an animal model (APP/PS1 mouse) of the Alzheimer's disease.
Figure 3:
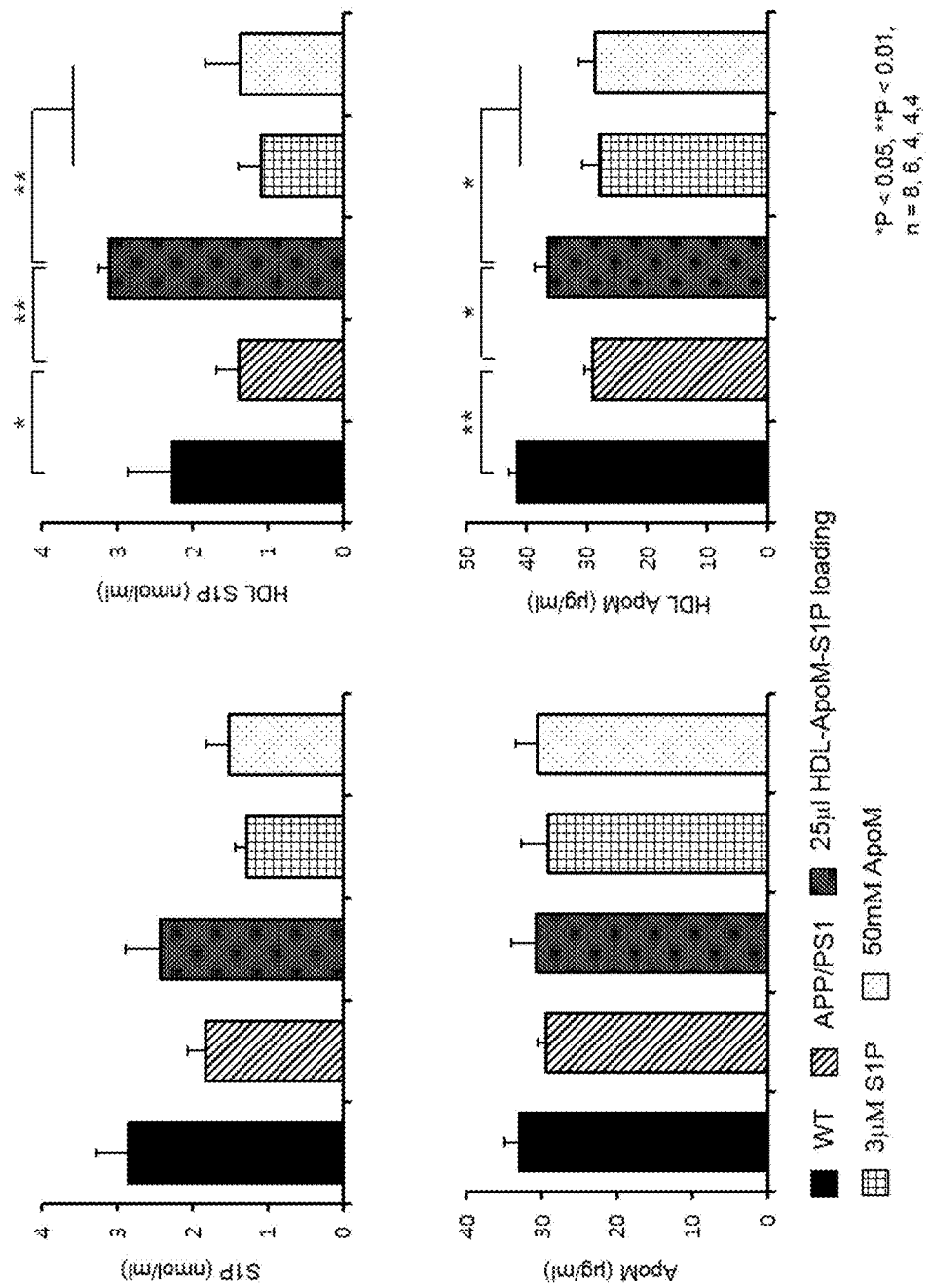
FIG. 3 shows the results of measuring the S1P, HDL-S1P, ApoM and HDL-ApoM levels in the plasma of WT (Wild Type, normal control mouse), APP/PS1 mice (an animal model of the Alzheimer's disease), APP/PS1 mice subjected to HDL-ApoM-S1P loading, APP/PS1 mice injected with S1P and APP/PS1 mice injected with ApoM.
Figure 4A:
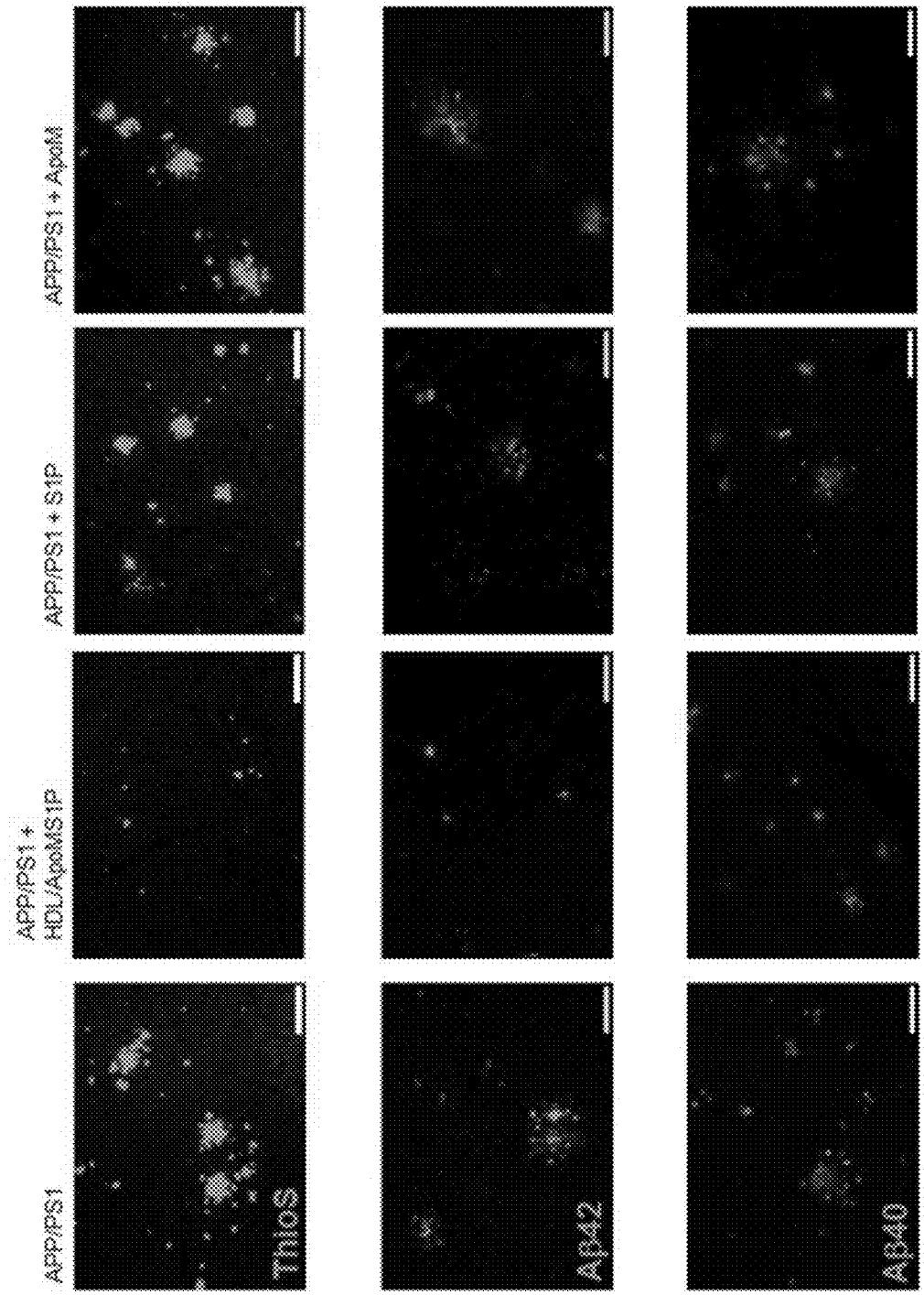
FIGS. 4a and 4b show the results of the amyloid-β deposition in the APP/PS1 mice (an animal model of the Alzheimer's disease), APP/PS1 mice subjected to HDL-ApoM-S1P loading, APP/PS1 mice injected with S1P and APP/PS1 mice injected with ApoM using thioflavin S, A1342 and A1340 staining, which show Microscopic images thereof (FIG. 4a) and quantitative results (FIG. 4b).
Figure 4B:
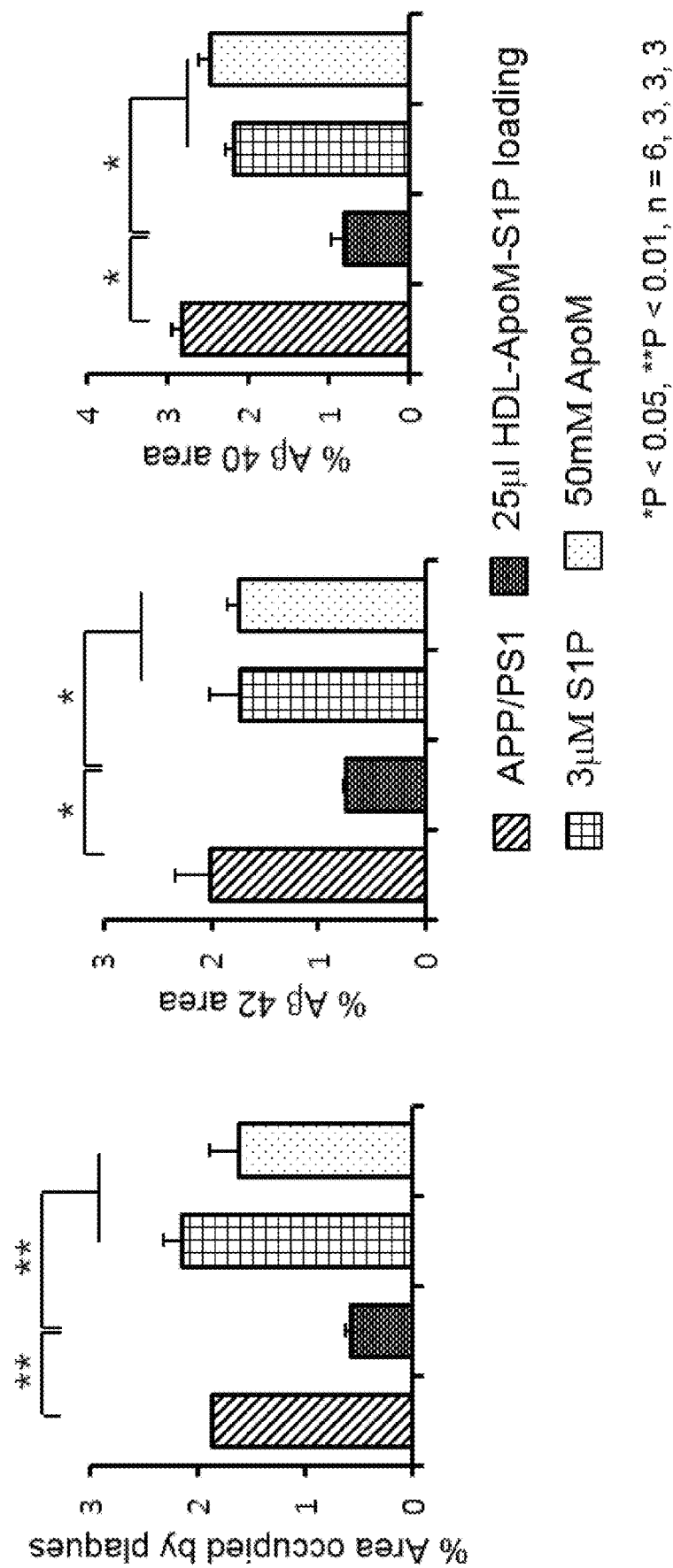
Figure 5A:
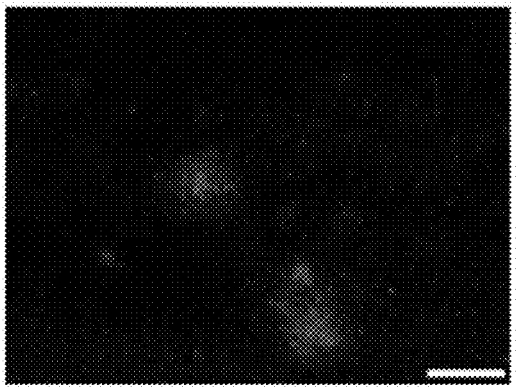
Figure 5A:
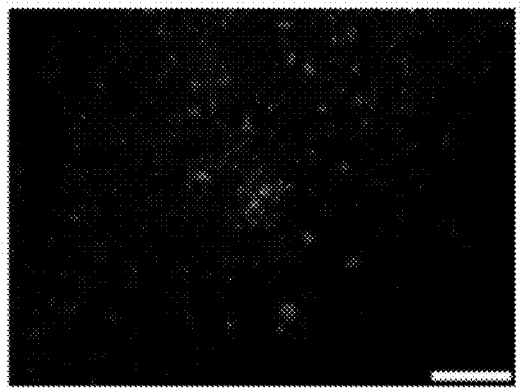
Figure 5A:
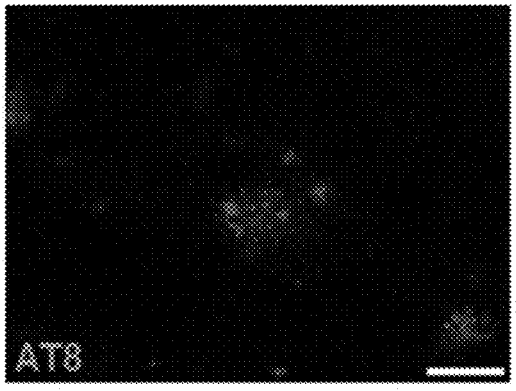
Figure 5A:
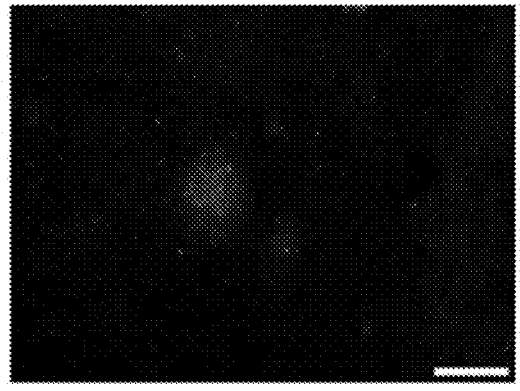
Figure 6A:
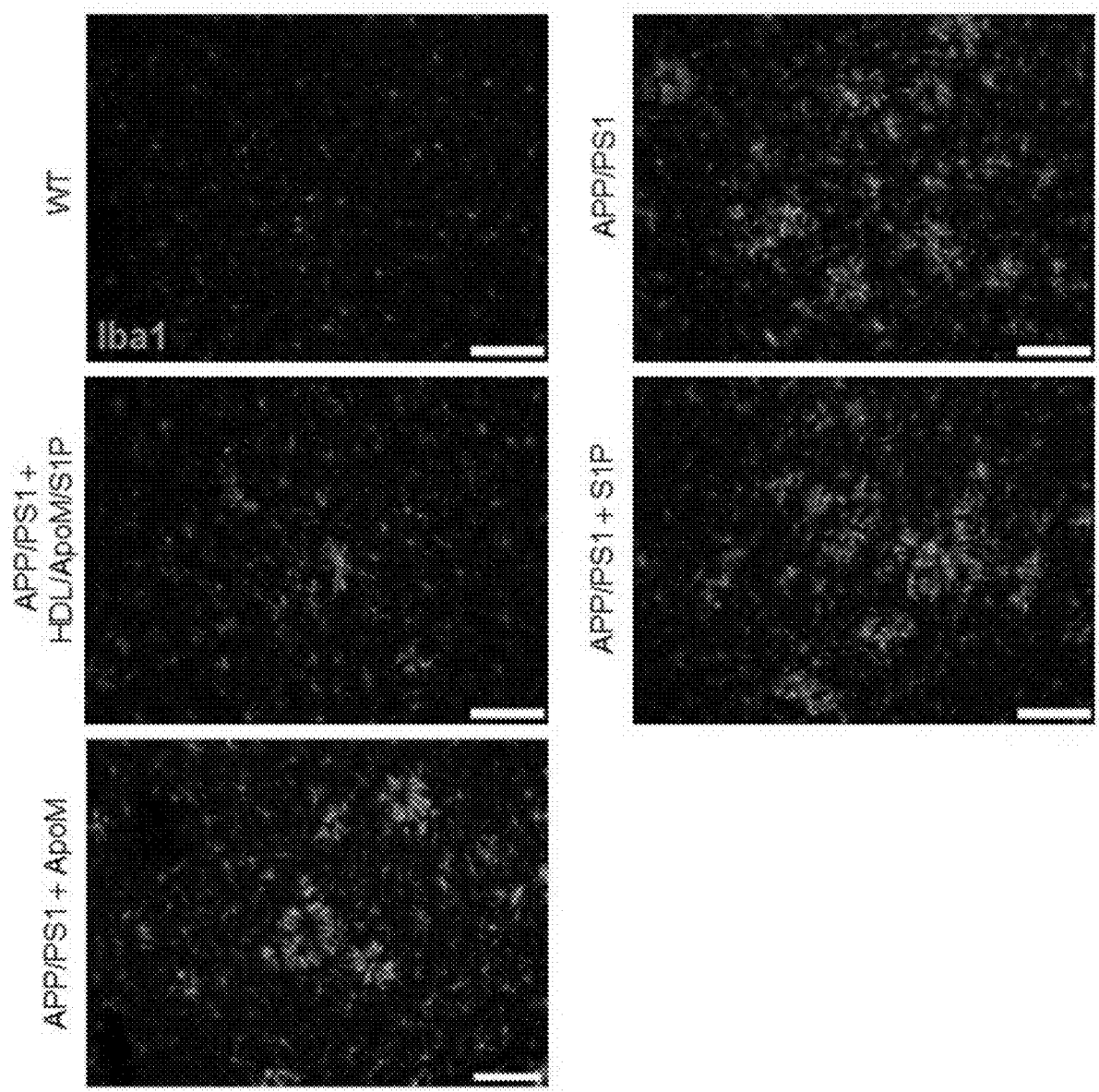
Figure 7A:
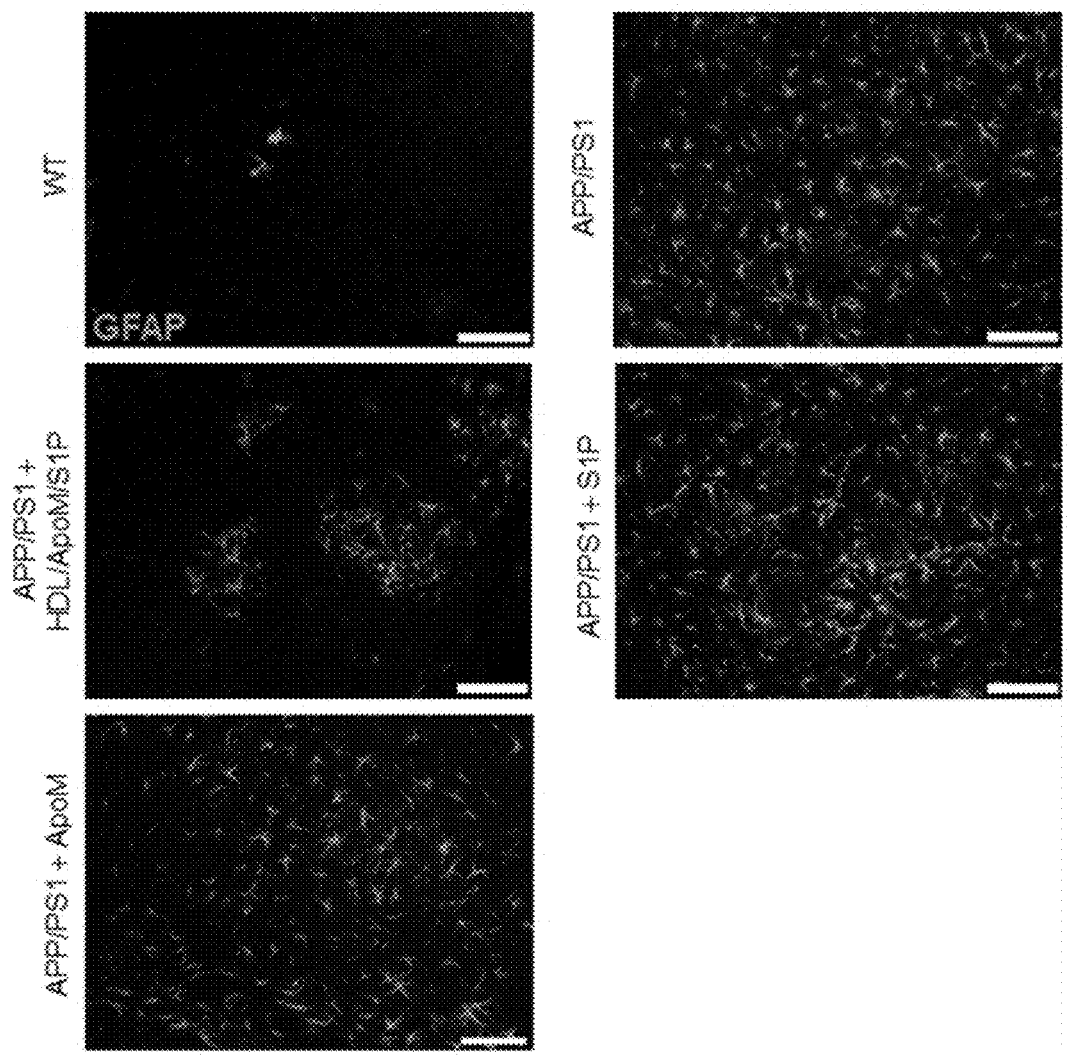

Example 1: Confirmation of the Treatment Effect on Alzheimer's Disease by HDL-ApoM-S1P Loading 1-1. Confirmation of HDL-ApoM-S1P Level after HDL-ApoM-S1P Loading in Plasma of Alzheimer's Mouse Models According to the experimental schedule shown in FIG. 2, HDL-ApoM-S1P loading was performed to APP/PS1 mice (Alzheimer's mouse models) through a total of 8 intravenous injections twice a week for 4 weeks. The results of measuring the levels of S1P and ApoM in the plasma of the mouse and in particular, the results of measuring the S1P and ApoM levels (i.e., HDL-S1P and HDL-ApoM) in the HDL fraction were shown in FIG. 3. As shown in FIG. 3, the levels of S1P and ApoM were increased in the plasma of APP/PS1 mice subjected to HDL-ApoM-S1P loading, and the levels of HDL-S1P and HDL-ApoM in the HDL fraction were also increased. These results showed significantly higher levels of S1P, ApoM, HDL-S1P and HDL-ApoM levels in untreated group APP/PS1 mouse plasma. However, the S1P, ApoM, HDL-S1P and HDL-ApoM levels of APP/PS1 mice injected with S1P and APP/PS1 mice injected with ApoM did not show a difference compared to untreated APP/PS1 mice.

Figure 1:
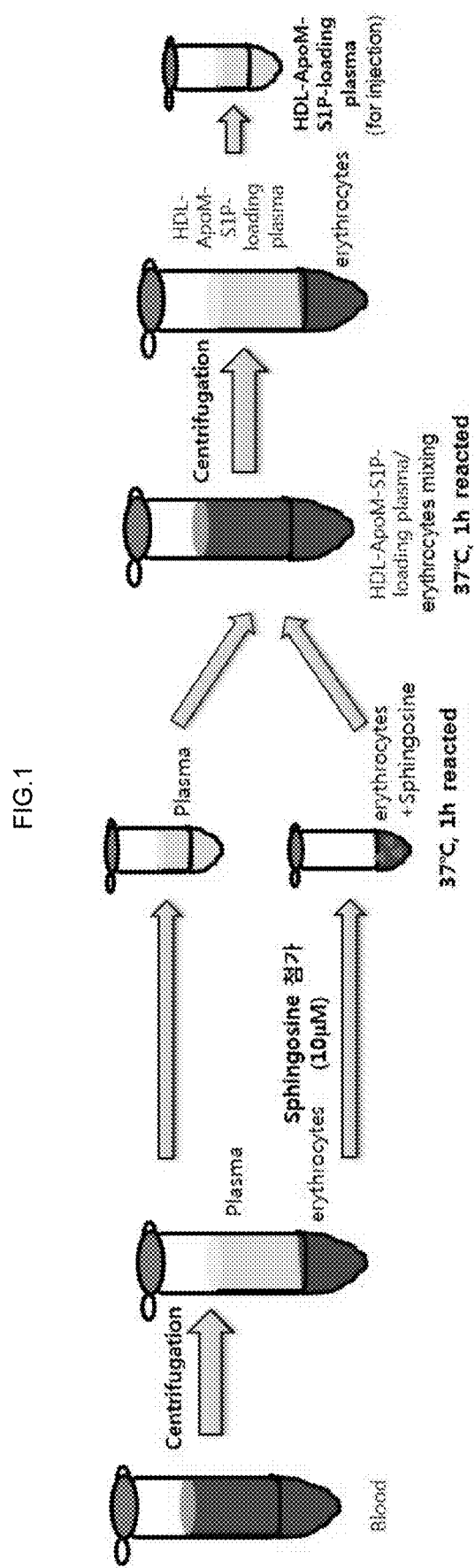
FIG. 1 is a schematic diagram showing the HDL-ApoM-S1P loading method.

Particularly in the case of ApoM, there was no significant difference in WT and untreated APP/PS1 mice in whole mouse plasma, but the HDL fraction showed significantly lower HDL-ApoM levels in untreated APP/PS1 mice compared to WT. In combination with the S1P and HDL-S1P results, this indicates that HDL-ApoM-S1P (HDL in which ApoM region is impregnated with S1P) was decreased in untreated group APP/PS1 mice. In contrast, HDL-ApoM-S1P levels in plasma of APP/PS1 mice loaded with HDL-ApoM-S1P were significantly higher compared to HDL-ApoM-S1P levels of plasma of APP/PS1 mice (see FIG. 3). In addition, when the HDL-ApoM-S1P loading in the experiment was considered to be injected again after treating the blood obtained from the individuals as shown in FIG. 1, HDL-ApoM level was remarkable increased. It is suggested that ApoM-S1P loading has a special relationship with ApoM.

1-2. Inhibition of Amyloid and Tau Deposition in the Brain after HDL-ApoM-S1P Loading in Plasma of Alzheimer's Mouse Models To determine the effect of HDL-ApoM-S1P loading on Alzheimer's disease, the amyloid and tau deposition in brain tissue (cerebral cortex) of each group of mice using thioflavin S staining and immunofluorescence were confirmed. The results of amyloid-β deposition using thioflavin S staining and immunofluorescence were shown in FIGS. 4a and 4b, and the results of tau deposition using immunofluorescence were shown in FIGS. 5a and 5b. As shown in FIGS. 4a, 4b, 5a, and 5b, APP/PS1 mice injected with S1P or ApoM did not show a significant difference compared to the brain tissue of the 9-month-old untreated group APP/PS1 mice. However, Aβ42, Aβ40 and tau (confirmation with AT8) were significantly decreased in brain tissues of APP/PS1 mice loaded with HDL-ApoM-S1P.

1-3. Confirmation of Neuroinflammatory Inhibition Effect of Alzheimer's Model by HDL-ApoM-S1P Loading To determine the effect of HDL-ApoM-S1P loading on neuroinflammatory responses, microglia and astrocytes in each experimental group were observed. The results of the activity of the microglia were shown in FIGS. 6a and 6b, and the results of the activity of the astrocytes were shown in FIGS. 7a and 7b. As shown in FIGS. 6a, 6b, 7a, and 7b, APP/PS1 mice injected with S1P or ApoM showed no significant difference compared to the brain tissues of untreated group APP/PS1 mice, but APP/PS1 mice loaded with S1P showed a significant decrease in the inflammatory activity of microglia and astrocytes.

Figure 8A:
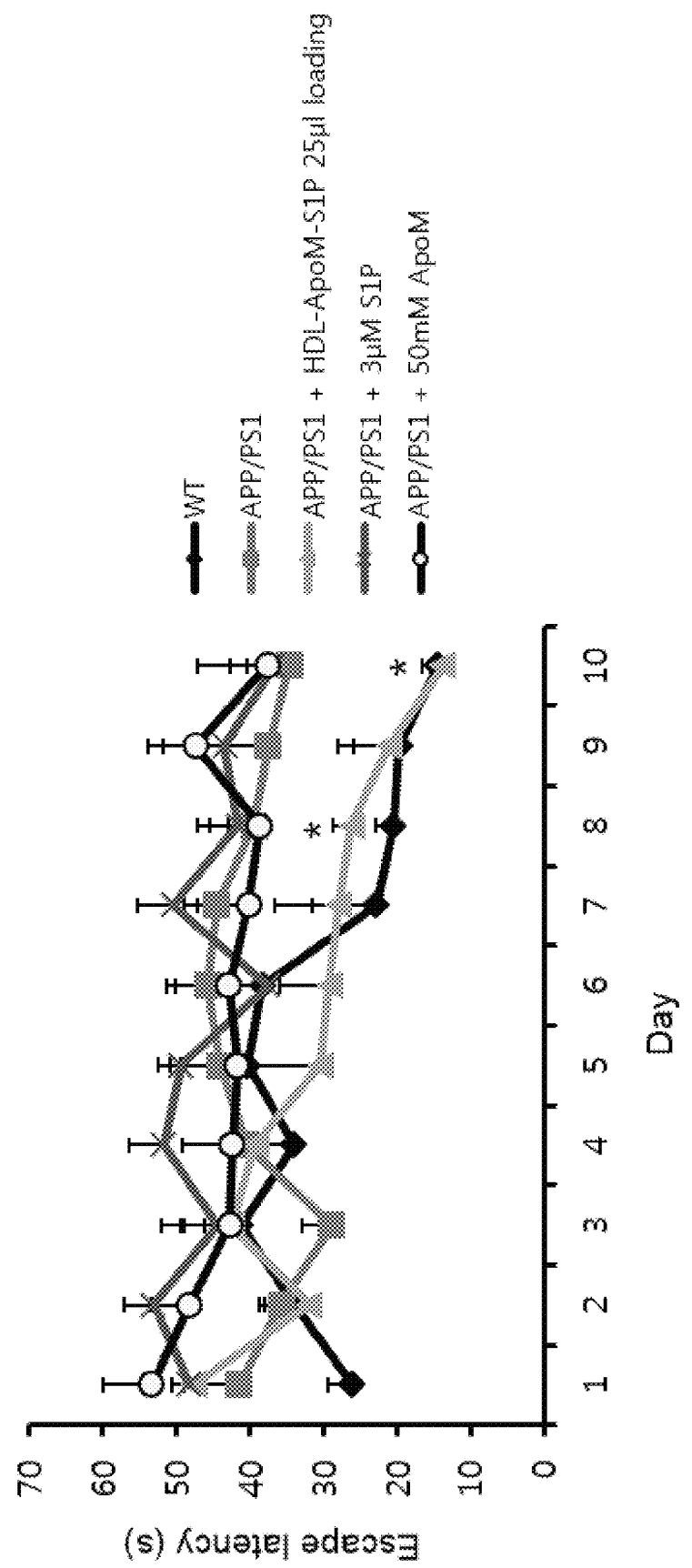
FIGS. 8a and 8b show the results of performing a Morris water maze (MWM) test in the WT (normal control mouse), APP/PS1 mice (an animal model of the Alzheimer's disease), APP/PS1 mice subjected to HDL-ApoM-S1P loading, APP/PS1 mice injected with S1P and APP/PS1 mice injected with ApoM, which show the results of the learning and memory assessment for 10 days (FIG. 8a) and the period of stay on the target platform on day 11 of the MWM test (FIG. 8b).
Figure 8B:
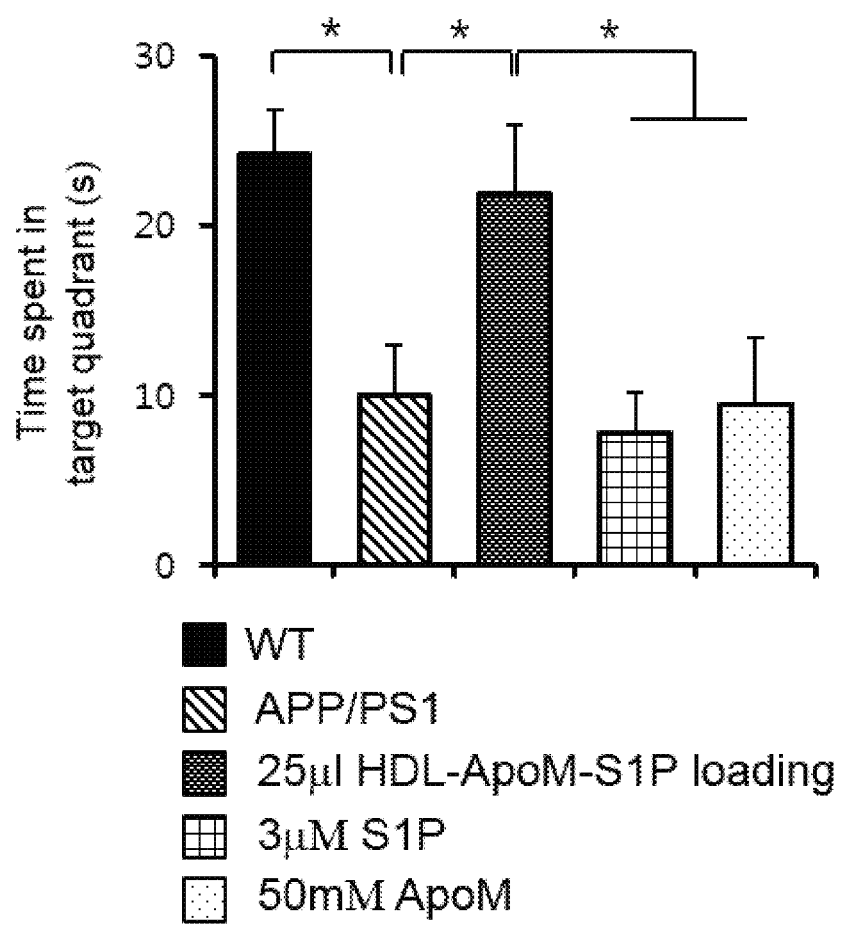
Figure 9:
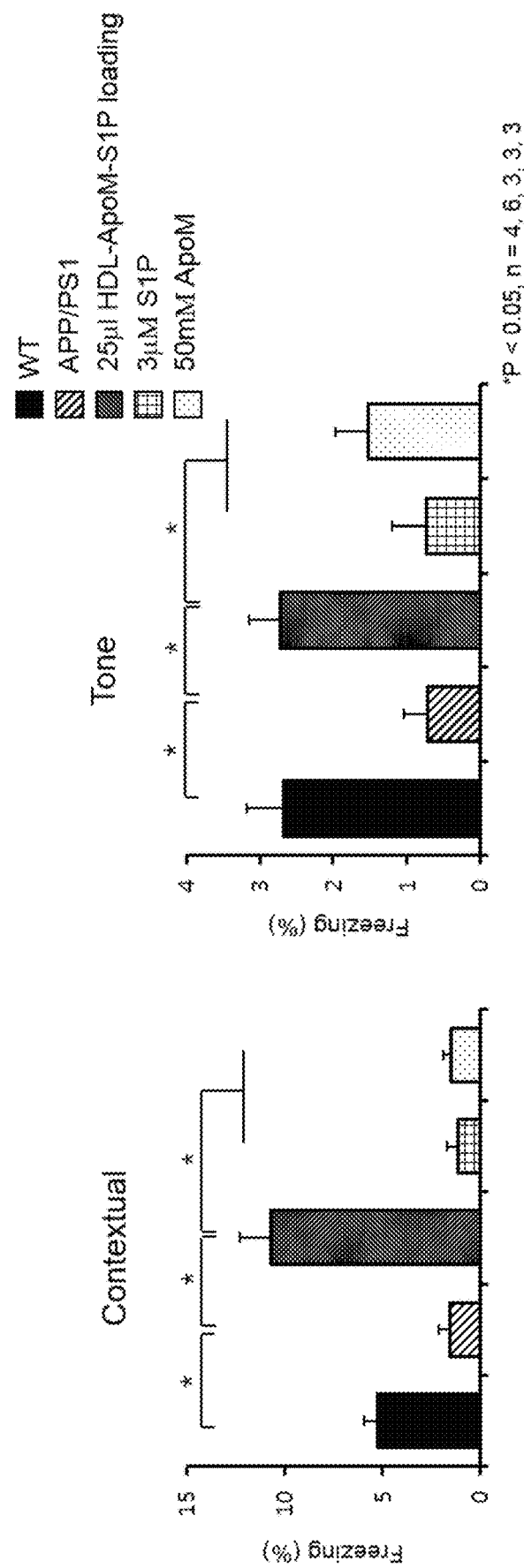
FIG. 9 shows the results of the contextual and tone tasks when fear conditioning is performed in the WT (normal control mouse), APP/PS1 mice (an animal model of the Alzheimer's disease), APP/PS1 mice subjected to HDL-ApoM-S1P loading.

1-4. Improvement of Learning and Memory Ability of Alzheimer's Model by HDL-ApoM-S1P Loading To determine the potential effect of increased HDL-ApoM-S1P on learning and memory by performing HDL-ApoM-S1P loading on plasma of APP/PS1 mice, MWM (Morris water maze) tests and Fear conditioning were performed. As shown in FIGS. 8a, 8b, and 9, untreated group APP/PS1 mice and APP/PS1 mice injected with S1P or ApoM showed severe impairment in spatial memory formation, but APP/PS1 mice loaded with HDL-ApoM-S1P were found to have significantly improved this impairment of learning and memory.

Example 2: The Treatment Effect of Alzheimer's Disease on Increase of Genetic HDL-ApoM-S1P It is further confirmed through the following experiment whether the HDL-ApoM-S1P of the present invention exhibits the effect in an ApoM dependent manner.

Figure 11:
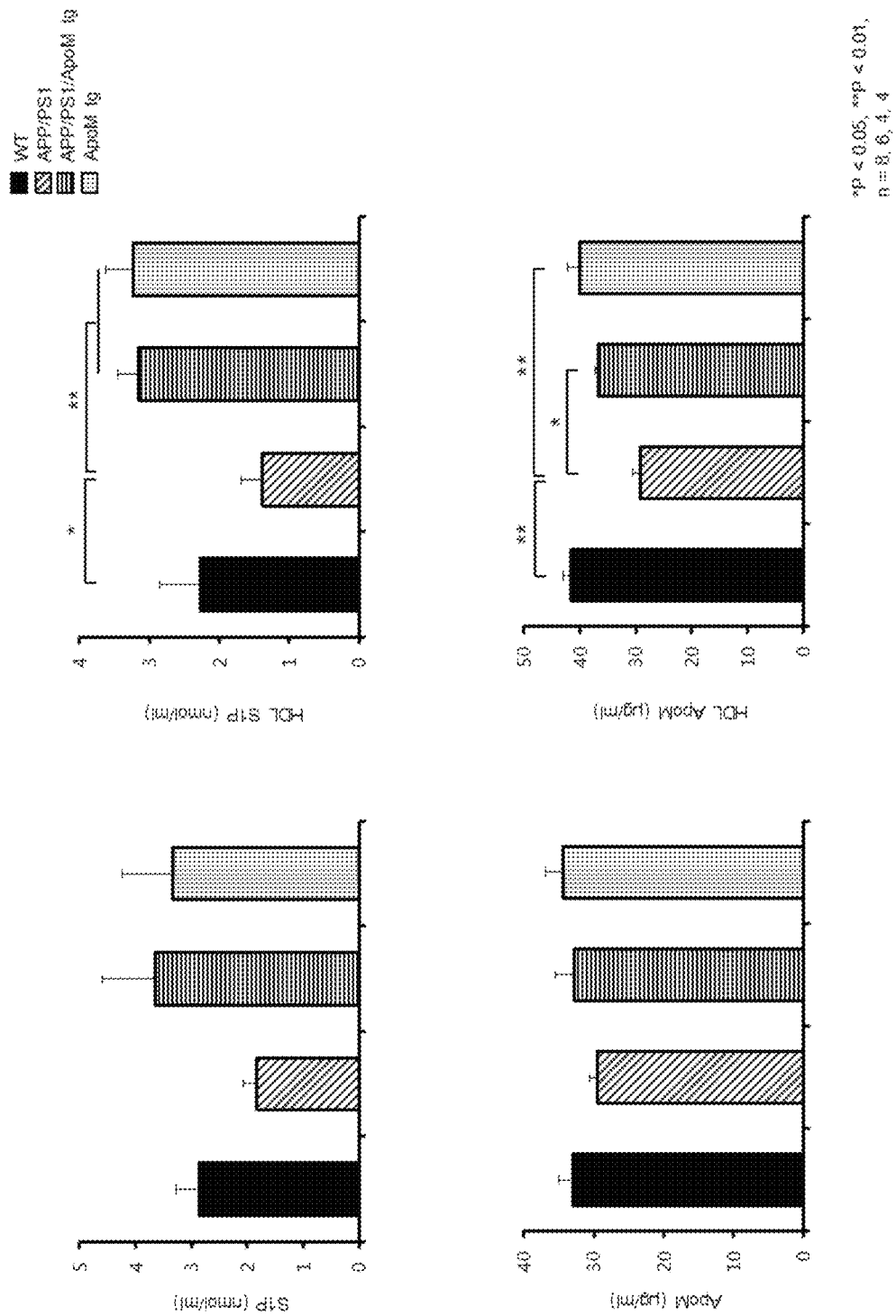
FIG. 11 shows the results of measuring S1P, HDL-S1P, ApoM and HDL-ApoM in plasma of the WT (Wild Type, normal control mice), ApoM tg (normal mice overexpressing ApoM), APP/PS1 (an animal model of the Alzheimer's disease) and APP/PS1/ApoM tg mice (an animal model of the Alzheimer's disease which is overexpressing ApoM).
Figure 12A:
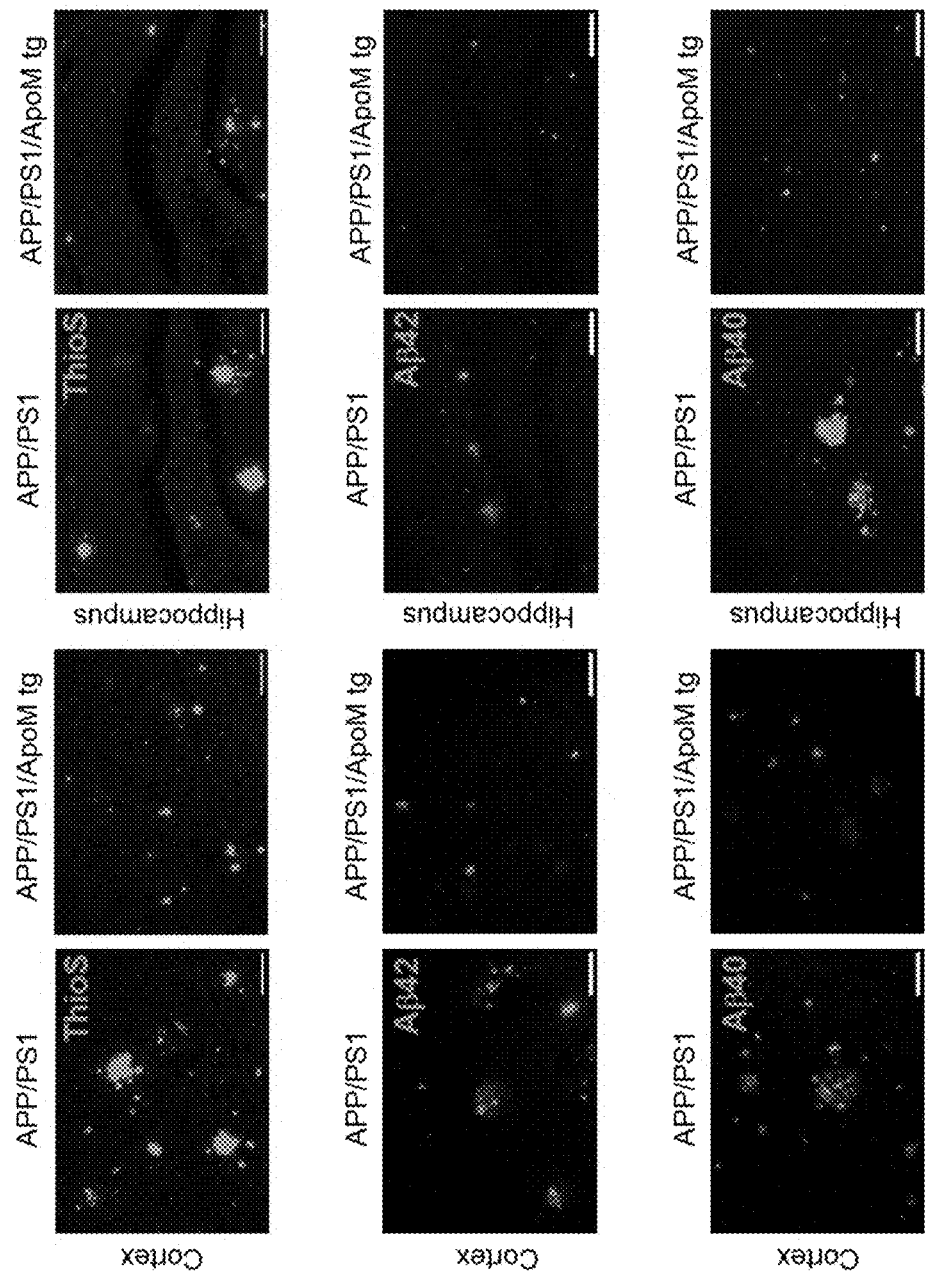
FIGS. 12a and 12b show the results of measuring the amyloid-β deposition in APP/PS1 mice and APP/PS1/ApoM tg mice using thioflavin S, Aβ42 and Aβ40 staining, which show Microscopic images thereof (FIG. 12a) and quantitative results (FIG. 12b).
Figure 12B:
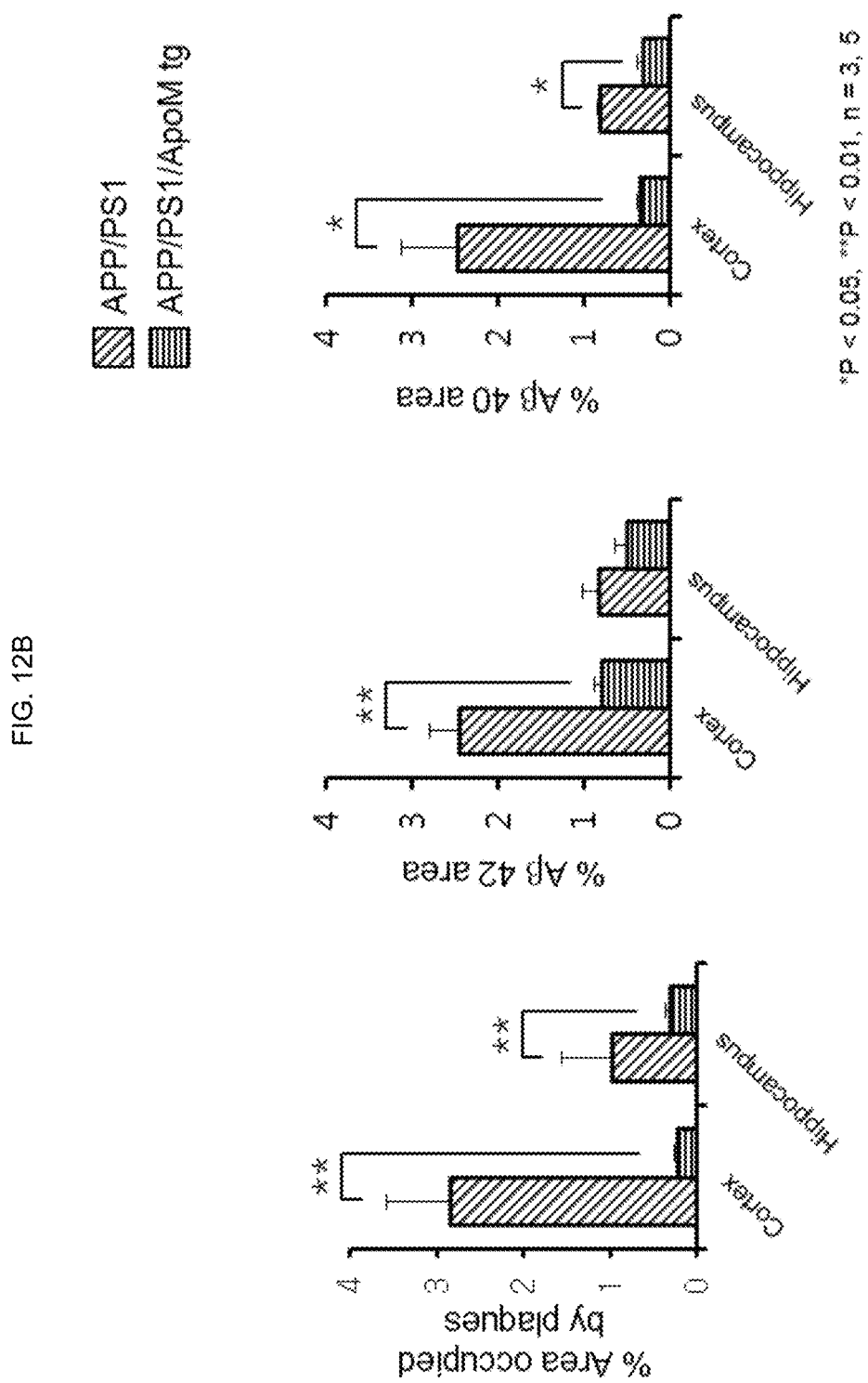
Figure 13A:
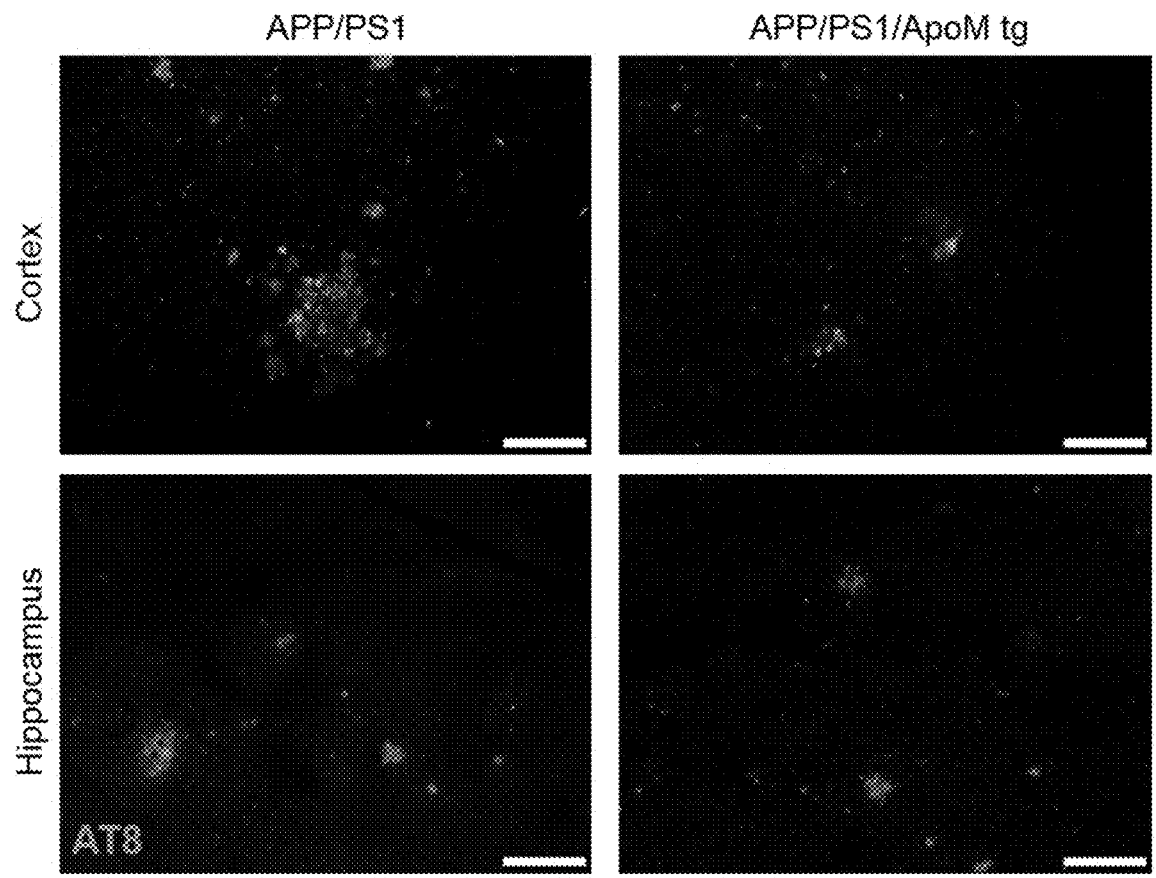
Figure 14A:
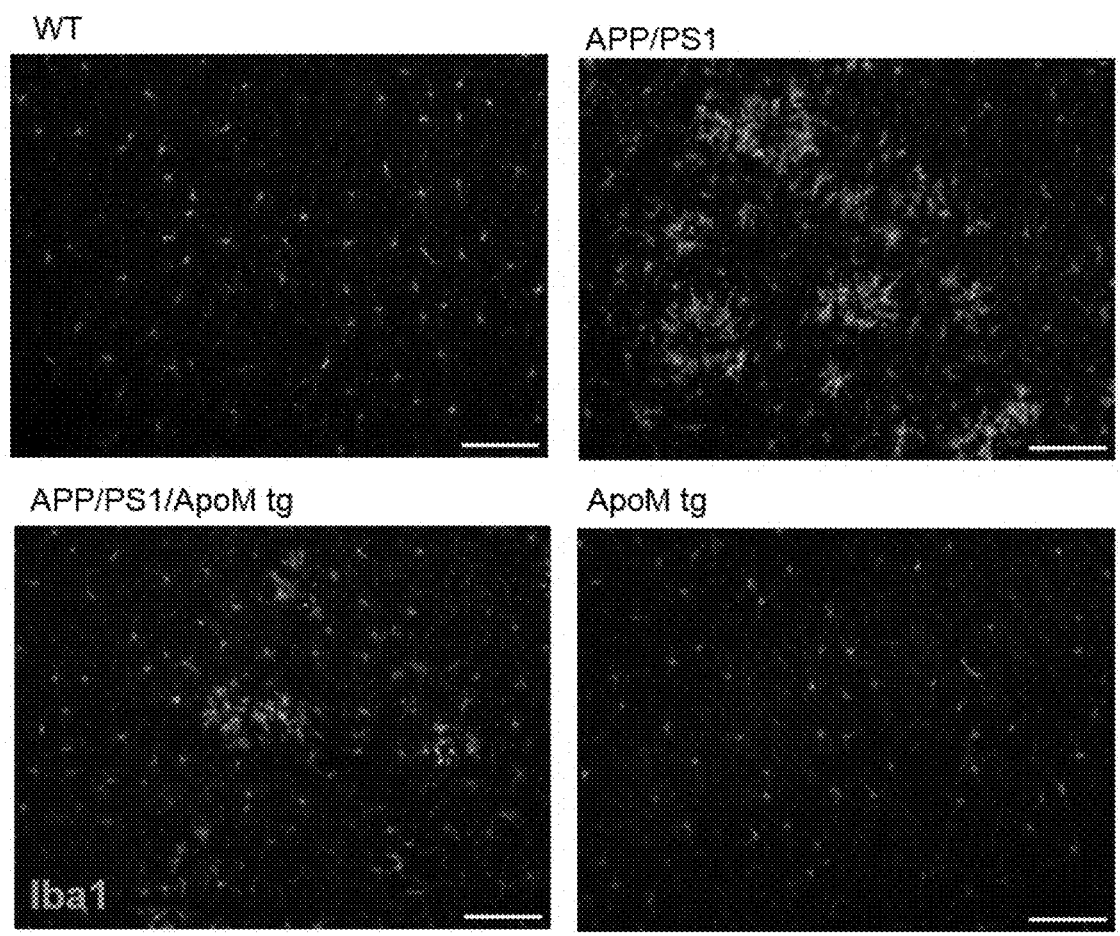
Figure 15A:
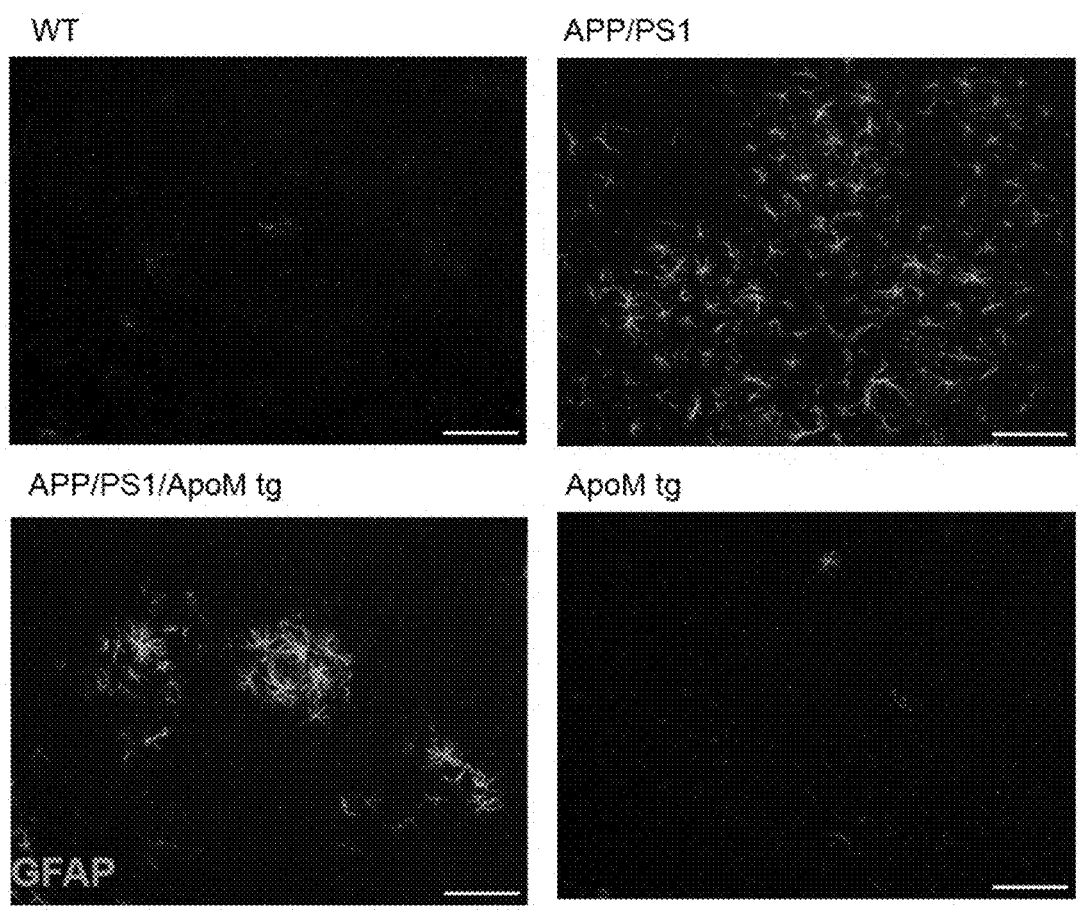

2-1. Comparison of HDL-ApoM-S1P Levels in Plasma of Alzheimer's Mouse Model (APP/PS1/ApoM tg) Transformed to Overexpress ApoM As shown in FIG. 10, APP/PS1 (APP/presenilin) double mutant mouse and APP/PS1/ApoM tg triple mutant mouse (HDL-ApoM-S1P overexpressing mouse) was prepared as Alzheimer's experimental animal models. The results of measuring S1P, HDL-S1P, ApoM and HDL-ApoM levels in the plasma of the mice are shown in FIG. 11. As shown in FIG. 11, it was confirmed that the HDL-ApoM-S1P level of plasma of APP/PS1 mice at 9 months of age is decreased compared to wild-type mice (WT). Compared to the level of HDL-ApoM-S1P in the plasma of APP/PS1 mice, it was confirmed that the level of HDL-ApoM-S1P in plasma of APP/PS1/ApoM tg mice at 9 months of age is significantly higher. It was confirmed that the level of HDL-ApoM-S1P was also higher in ApoM tg mice.

2-2. Inhibition of Amyloid and Tau Deposition by increase of Genetic HDL-ApoM-S1P To determine the effect of increase of HDL-ApoM-S1P on Alzheimer's disease in APP/PS1/ApoM tg mice, the deposition of amyloid and tau in brain tissue (cerebral cortex and hippocampus) of each mouse experimental group was confirmed using thioflavin S staining and immunofluorescence. The results of amyloid-β deposition using thioflavin S staining and immunofluorescence were shown in FIGS. 12a and 12b, and the results of tau deposition using immunofluorescence were shown in FIGS. 13a and 13b. As shown in FIGS. 12a, 12b, 13a, and 13b, Aβ42 and Aβ40 and tau (identified as AT8) deposited on the brain tissues of APP/PS1/ApoM tg mice were significantly decreased compared to the brain tissues of APP/PS1/ApoM tg mice at 9 months of age.

2-3. Effects of Neuro-Inflammatory Inhibition in APP/PS1 Mice on Increase of Genetic HDL-ApoM-S1P In order to determine the effect of increased HDL-ApoM-S1P on the neuroinflammatory response in plasma of APP/PS1/ApoM tg mice, the present inventors observed the changes of microglia and astrocytes in each mouse experimental group. The results of the activity of the microglia were shown in FIGS. 14a and 14b, and the results of the activity of the astrocytes were shown in FIGS. 15a and 15b. As shown in FIGS. 14a, 14b, 15a, and 15b, it was confirmed that ApoM tg mice showed the same pattern as WT, but APP/PS1 mice had significant inflammatory activity in microglia and astrocytes compared to WT and ApoM tg mice. In contrast, APP/PS1/ApoM tg mice showed a significant decrease in the inflammatory activity of microglia and astrocytes compared with APP/PS1 mice.

Figure 16A:
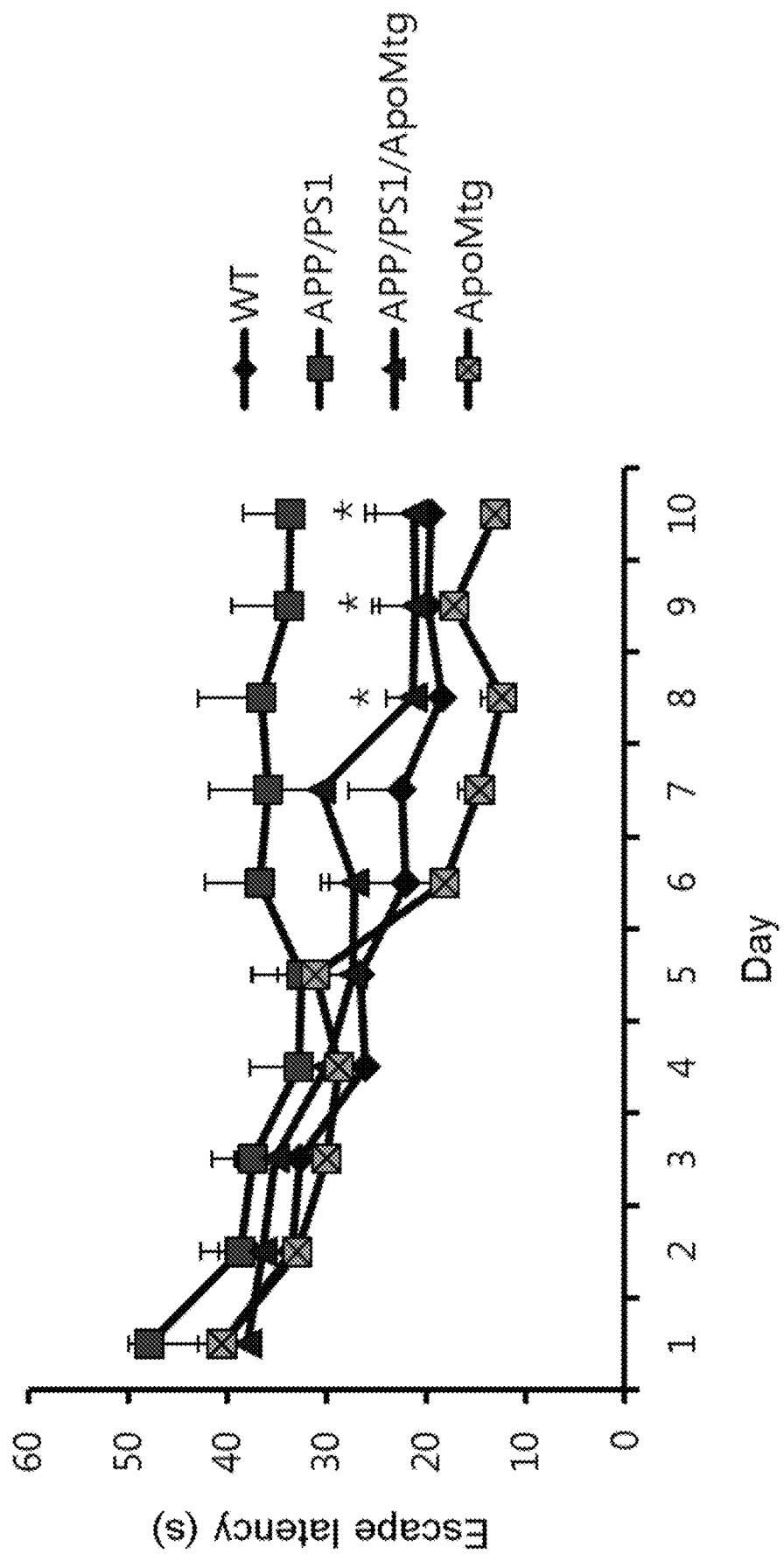
FIGS. 16a and 16b show the results of performing a Morris water maze (MWM) test in the WT (Wild Type, normal control mice), ApoM tg (normal mice overexpressing ApoM), APP/PS1 (an animal model of the Alzheimer's disease) and APP/PS1/ApoM tg mice, which show the results of the learning and memory assessment for 10 days (FIG. 16a) and the period of stay on the target platform on day 11 of the MWM test (FIG. 16b).
Figure 16B:
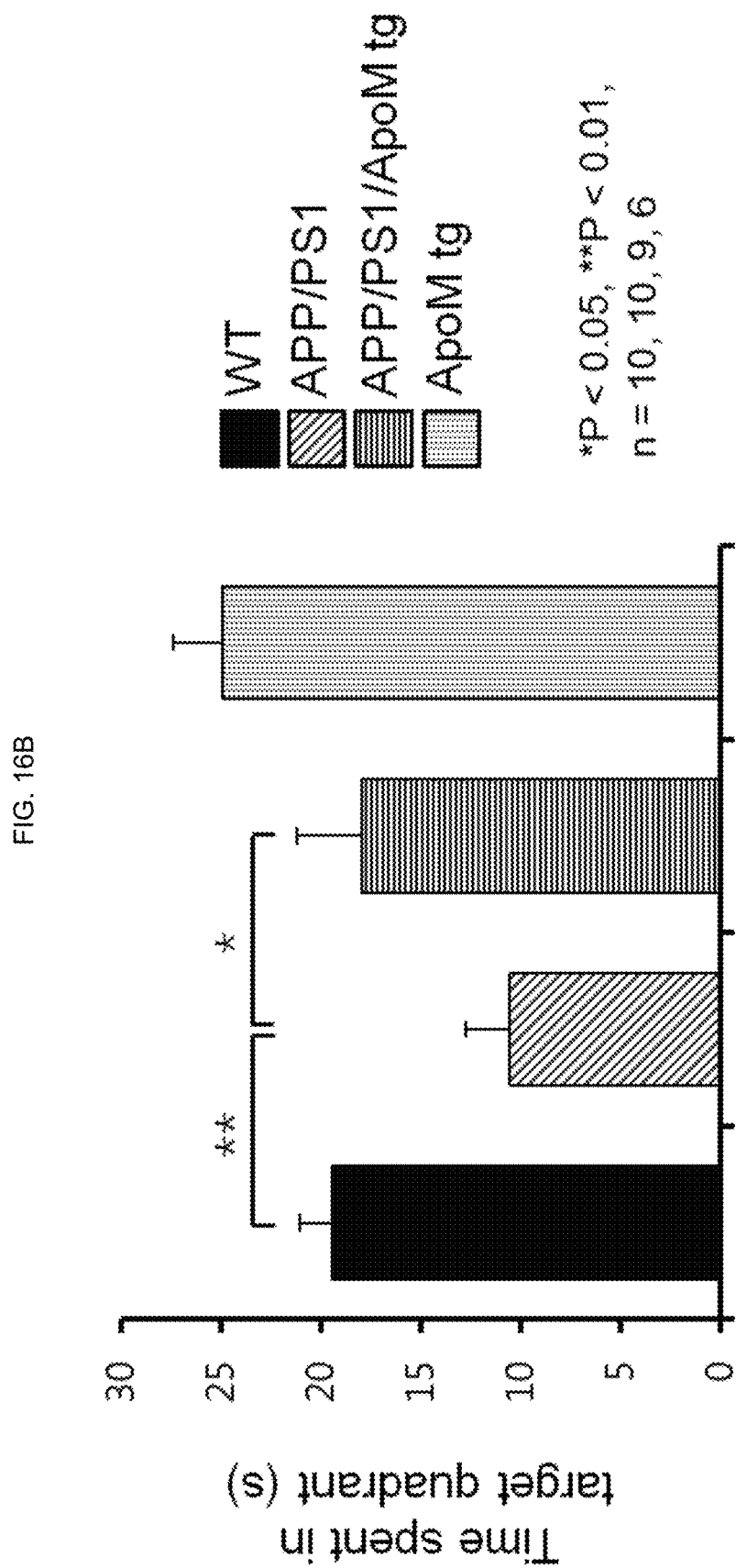
Figure 17:
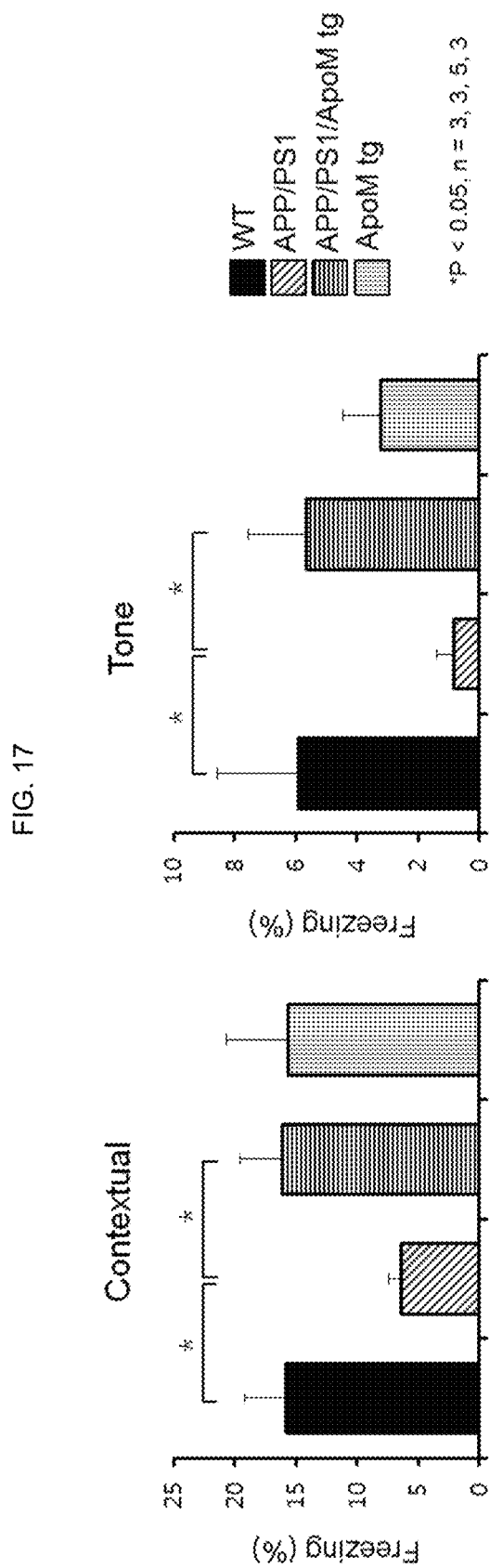
FIG. 17 shows the results of the contextual and tone tasks when fear conditioning is performed in the WT (Wild Type, normal control mice), ApoM tg (normal mice overexpressing ApoM), APP/PS1 (an animal model of the Alzheimer's disease) and APP/PS1/ApoM tg mice.

2-4. Improvement of Learning and Memory Ability by Increase of Genetic HDL-ApoM-S1P To identify potential effects of genetic HDL-ApoM-S1P on learning and memory, Morris water maze (MWM) tests and Fear conditioning were performed. As shown in FIGS. 16a, 16b, and 17, APP/PS1 mice showed severe impairment in spatial memory formation, and APP/PS1/ApoM tg mice were found to have greatly improved this impairment of learning and memory. In addition, as shown in FIGS. 16a and 16b, it was confirmed that ApoM tg mice had better cognition, learning, and memory than the WT group. These results suggest that the increased HDL-ApoM-S1P in plasma can help improve cognitive, learning and memory in normal individuals as well as in individuals with Alzheimer's disease), cognitive disorders, learning disabilities, and memory disorders.

INDUSTRIAL APPLICABILITY

The present invention relates to a novel use for HDL-ApoM-S1P (a high density lipoprotein in which apolipoprotein M is impregnated with sphingosine-1-phosphate), and more particularly, to using HDL-ApoM-S1P to prevent, improve, or treat degenerative brain disorders (in particular, Alzheimer's), cognitive disorders, learning disabilities, and memory disorders, and using HDL-ApoM-S1P to improve cognitive ability, learning ability, and memory.

The HDL-ApoM-S1P according to the present invention not only alleviates neuroinflammation but also significantly exhibits improvement effects of cognitive disorder, learning disability, and memory disorder with respect to individuals suffering from degenerative brain disorders (in particular, Alzheimer's), and exhibits an effect of greatly reducing amyloid beta and tau deposition. Moreover, increased HDL-ApoM-S1P in the body also has an excellent effect of improving the cognitive, learning, and memory abilities of non-disabled individuals, which is highly likely to be used industrially.

What is claimed is:

1. A method for treating Alzheimer's disease, the method comprising administering an effective amount of a composition comprising a high density lipoprotein (HDL-ApoM-S1P) in which apolipoprotein M is impregnated with sphingosine-1-phosphate as an active ingredient to an individual in need thereof.

2. A method for treating Alzheimer's disease associated cognitive disorders, learning disabilities, and memory disorders, the method comprising administering an effective amount of a composition comprising a high density lipoprotein (HDL-ApoM-S1P) in which apolipoprotein M is impregnated with sphingosine-1-phosphate as an active ingredient to an individual in need thereof.

* * * * *